United States Patent
Kotsbak

(10) Patent No.: US 11,549,141 B2
(45) Date of Patent: Jan. 10, 2023

(54) METHOD OF SEQUENCING IMMOBILIZED POLYNUCLEOTIDES

(71) Applicant: GeneSeque AS, Trondheim (NO)

(72) Inventor: Jarle Kotsbak, Trondheim (NO)

(73) Assignee: GENESEQUE AS, Trondheim (NO)

( * ) Notice: Subject to any disclaimer, the term of this patent is extended or adjusted under 35 U.S.C. 154(b) by 277 days.

(21) Appl. No.: 15/501,962

(22) PCT Filed: Jul. 31, 2015

(86) PCT No.: PCT/EP2015/067709
§ 371 (c)(1),
(2) Date: Feb. 6, 2017

(87) PCT Pub. No.: WO2016/020292
PCT Pub. Date: Feb. 11, 2016

(65) Prior Publication Data
US 2021/0381044 A1    Dec. 9, 2021

(30) Foreign Application Priority Data
Aug. 6, 2014    (GB) ...................................... 1413929

(51) Int. Cl.
*C12Q 1/6874*    (2018.01)
*C12Q 1/6837*    (2018.01)

(52) U.S. Cl.
CPC ......... *C12Q 1/6874* (2013.01); *C12Q 1/6837* (2013.01)

(58) Field of Classification Search
None
See application file for complete search history.

(56) References Cited

U.S. PATENT DOCUMENTS

| 5,714,330 A | 2/1998 | Brenner et al. |
| 5,843,651 A | 12/1998 | Stimpson et al. |
| 7,323,305 B2 | 1/2008 | Leamon et al. |

(Continued)

FOREIGN PATENT DOCUMENTS

| CN | 101245390 | 8/2008 |
| EP | 0 330 185 | 8/1989 |

(Continued)

OTHER PUBLICATIONS

Edelstein et al., "The BARC biosensor applied to the detection of biological warfare agents", Biosensors & Bioelectronics, 14(10-11): 805-813 (2000).

(Continued)

*Primary Examiner* — Kaijiang Zhang
(74) *Attorney, Agent, or Firm* — Wenderoth, Lind & Ponack, L.L.P.

(57) ABSTRACT

The present invention concerns a method of sequencing immobilized polynucleotides in which beads which are tethered to the solid support are used as labels to identify bases within the polynucleotides. The beads carry sets of probes or bases which can bind to the polynucleotide allowing identification of the target base(s). Identification of the base(s) is achieved through sequential application of different cleavage means specific to different probes/bases carried on the beads. Also provided is an apparatus for performing the method and a kit comprising the apparatus and other components necessary for performing the method.

Figure 1:
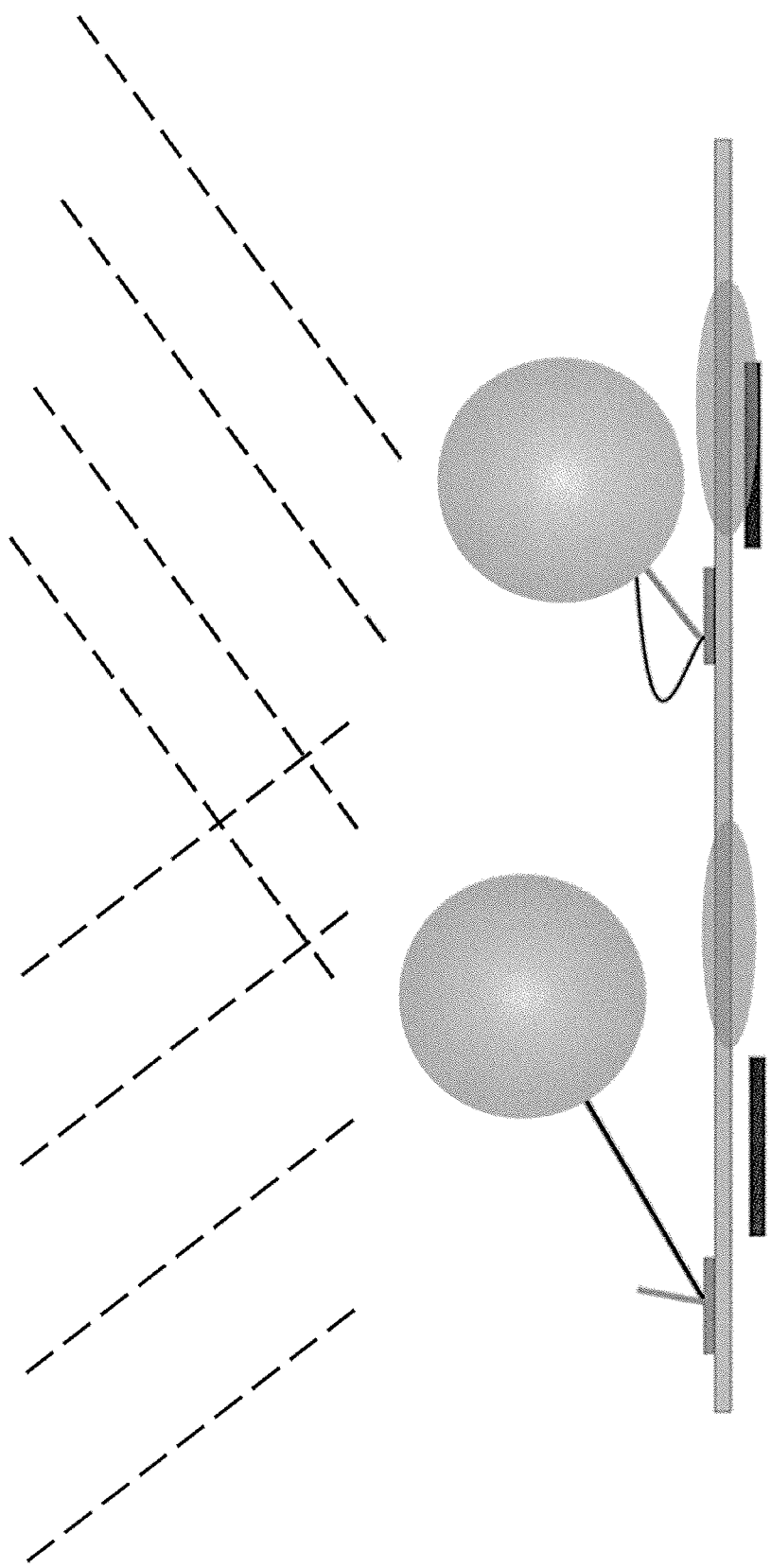

20 Claims, 6 Drawing Sheets
Specification includes a Sequence Listing.

(56) References Cited

U.S. PATENT DOCUMENTS

| | | |
|---|---|---|
| 2002/0168663 A1 | 11/2002 | Phan et al. |
| 2003/0215825 A1 | 11/2003 | Tong |
| 2003/0224439 A1 | 12/2003 | Lafferty et al. |
| 2005/0087000 A1 | 4/2005 | Coehoorn et al. |
| 2005/0244863 A1 | 11/2005 | Mir |
| 2005/0250094 A1 | 11/2005 | Storhoff et al. |
| 2006/0084069 A1 | 4/2006 | Chan et al. |
| 2006/0127942 A1 | 6/2006 | Straume et al. |
| 2008/0182235 A1 | 7/2008 | Hearn et al. |
| 2008/0207464 A1 | 8/2008 | Prins et al. |
| 2008/0311561 A1 | 12/2008 | Ahn et al. |
| 2009/0036323 A1 | 2/2009 | van Eijk et al. |
| 2009/0048124 A1 | 2/2009 | Leamon et al. |
| 2009/0062129 A1 | 3/2009 | McKernan et al. |
| 2010/0009354 A1* | 1/2010 | Nagai et al. ......... C12Q 1/6869 435/6.16 |
| 2010/0035252 A1 | 2/2010 | Rothberg et al. |
| 2010/0120132 A1 | 5/2010 | Koo |
| 2010/0323355 A1 | 12/2010 | Dittmer |
| 2011/0008775 A1 | 1/2011 | Gao et al. |
| 2011/0171749 A1 | 7/2011 | Alocilja et al. |

FOREIGN PATENT DOCUMENTS

| | | |
|---|---|---|
| EP | 0 703 991 | 5/2001 |
| JP | 2002-85097 | 3/2002 |
| WO | 2007/092941 | 8/2007 |
| WO | 2009/024781 | 2/2009 |
| WO | 2010/016937 | 2/2010 |
| WO | 2010/109159 | 9/2010 |
| WO | 2012/042052 | 4/2012 |
| WO | 2012/042053 | 4/2012 |
| WO | WO-2012042052 A1 * | 4/2012 ........... C12Q 1/6874 |
| WO | 2014/033285 | 3/2014 |

OTHER PUBLICATIONS

International Search Report and the Written Opinion of the International Searching Authority, dated Oct. 9, 2015 in corresponding International Application No. PCT/EP2015/067709.

Aylur, Turgut et al., "A novel magnetic bead bioassay platform using a microchip-based sensor for infectious disease diagnosis", Journal of Immunological Methods, 2006, vol. 314, pp. 21-29.

Brenner, Sydney et al., "Gene expression analysis by massively parallel signature sequencing (MPSS) on microbead arrays", Nature Biotechnology, Jun. 2000, vol. 18, pp. 630-634.

Fuller, Carl W. et al., "The challenges of sequencing by synthesis", Nature Biotechnology, Nov. 2009, vol. 27, No. 11, pp. 1013-1023.

Mulvaney, S.P. et al., "Rapid, femtomolar bioassays in complex matrices combining microfluidics and magnetoelectronics", Biosensors and Bioelectronics, 2007, vol. 23, pp. 191-200.

Shlyapnikov, Yury M. et al., "Detection of microarray-hybridized oligonucleotides with magnetic beads", Analytical Biochemistry, 2010, vol. 399, pp. 125-131.

Stahl, Patrik L. et al., "Visual DNA—Identification of DNA sequence variations by bead trapping", Genomics, 2007, vol. 90, pp. 741-745.

\* cited by examiner

METHOD OF SEQUENCING IMMOBILIZED POLYNUCLEOTIDES

A sequence listing in electronic (ASCII text file) format is filed with this application and incorporated herein by reference. The name of the ASCII text file is "2017_0150A_ST25.txt"; the file was created on Jun. 22, 2020; the size of the file is 3 KB.

The present invention concerns new methods of sequencing polynucleotides in which beads which are tethered to the solid support are used as labels to identify bases within the polynucleotides.

Polynucleotide sequencing has been carried out by various methods for many years and has provided a mine of information concerning the genomes of different species. Even though the human genome has been sequenced, there is a great interest in sequencing in order to identify genetic predispositions or genetic or gene related diseases. Hence, the mapping of mutations and tissue specific mRNA production and expression analysis is of great interest. Additionally, the sequencing of genomes from other species is of interest i.e. de novo sequencing.

DNA sequencing has been traditionally carried out by the Sanger dideoxy method (Sanger, Nicklen and Coulson, Proc. Natl. Acad. Sci. USA, 1977, 74, 5463-7) which has been used since the 1980s. It is a multimolecular method based on electrophoretic filtering of cloned DNA that is firstly treated enzymatically. The enzymatic process produces single stranded DNA by interrupted polymerisation using a mixture of fluorophore labelled dideoxy NTPs which terminate chain extension and dNTPs which do not. Hence, a mixture of chain lengths is obtained using this process where the length of each DNA strand represents the base position and the colour of the connected fluorophore represents the identity of the base at the 3' end. These identities are read as aligned coloured dots, with one line of dots representing one DNA sequence. However, the Sanger sequencing method requires the use of multiple chains and sequencing is possible of only about 1000 bases.

The chemical degradation method of Maxam et al (Proc. Natl. Acad. Sci., 1977, 74, 560-4) has also been used for DNA sequencing and involves the cleavage of a nucleotide sequence at specific nucleotides, resulting in the production of chains of different lengths where each length is indicative of the presence of a particular nucleotide at that position. Thus the chemical degradation method also requires electrophoretic separation of strands for sequence determination.

Both the chain termination method of Sanger and the chemical degradation method of Maxam therefore require the generation of one or more sets of labelled DNA fragments, which each terminate with a particular nucleotide base. The fragments must be separated by size to determine the sequence and thus the electrophoretic gels used must be able to distinguish large fragments which differ in size by a single nucleotide. As discussed above, this limits the size of the DNA chain that can be sequenced at one time.

Modifications to the chain termination method have been proposed in the art, for example by combining the enzymatic and readout phases. Thus, instead of a base position being represented by a position on an electrophoretic filter, the base position is provided by a reading taken at a particular point in time. The sequence can therefore be read in realtime. The first technology to use this principle, namely pyrosequencing (Ronaghi, Uhlen and Nyren, Science, 1998, 281, 363-365), does not use fluorophores but luciferase that produces light when triggered indirectly by pyrophosphate released from a polymerisation step where nucleotides are supplied one at a time. The yield of light from this process is much lower than with fluorophores, thus DNA must still be cloned such that each polymerisation step yields enough light for secure detection. This method may process DNA lengths of 400 nucleotides but is not well suited for detecting homopolymers within sequences i.e. repetitions of the same nucleotide.

Other realtime methods include sequencing by synthesis which can be used for multimolecule or single molecule sequencing, sequencing by ligation (for multimolecule sequencing) and sequencing by stepwise ligation and cleavage (for multimolecule sequencing). Sequencing by synthesis involves the use of fluorophore labelled terminating nucleotide bases which are added to an immobilised target DNA sequence. A single terminating nucleotide base is thus incorporated by polymerisation into the target DNA sequence in each cycle and the base is then determined by virtue of its fluorophore label. The terminating base can be chemically neutralised once the readout has been obtained to allow polymerisation to continue. Further, the lipid chain between the base and the label can be cleaved chemically or photochemically so that previously incorporated labels can be removed to allow the reading of subsequently incorporated labels.

Sequencing by ligation involves ligating fluorophore labelled probes to an unknown sequence where the sequence can be determined by the sequence of the probe which is able to ligate thereto. Further, sequencing by stepwise ligation and cleavage (Brenner et al, U.S. Pat. No. 5,714,330, which is incorporated herein by reference) involves a collection of slightly varied methods, based on the use of a probe which has a nuclease recognition site for a nuclease whose cleavage site is separate from the recognition site. Thus, the DNA sequence may be determined either by virtue of the sequence of the probe which binds thereto or by virtue of a label attached to a nucleotide base incorporated into the DNA sequence and the nuclease recognition site in the probe is then able to induce cleavage of the DNA sequence to be determined to release the probe and/or incorporated nucleotide to shorten the sequence to allow determination of the next nucleotide(s).

However, none of the sequencing methods described above are without their limitations. Several of the methods result in "dephasing" or asynchronism which produces smearing of results which limits the length of the chains which may be sequenced. Other methods have long read times. The alternatives tried in the art to address these limitations require the use of expensive equipment such as high numeric aperture laser scanning confocal microscopes or are limited to reading short sequences due to stalling, which occurs due to the use of modified nucleotides. A sequencing method is therefore required which does not require the use of expensive equipment and is able to sequence long chains.

The use of beads as labels in sequencing reactions is known, see for example (WO2012/042052). The use of beads as labels in the sequencing reaction provides many advantages over the traditional use of fluorophore labels. Firstly, beads are easy to detect since they are larger than fluorophores which enables their use in single molecule sequencing. Furthermore, there is no problem with low signal level when using beads as labels. Further, beads may be detected without the use of expensive equipment, for example using an electronic bead detection mechanism in an integrated circuit or based on light or magnetism. Beads are easily and rapidly removed from a reaction, particularly if they are paramagnetic and hence there is no problem with noise when using bead labels, as opposed to fluorescent labels. Furthermore, mechanical cleavage may be used thus avoiding chemical removal as required in some prior art sequencing methods.

However, the use of beads which are attached via a tether to a solid support and which carry the probes/bases to be used in the sequencing reaction have not been described previously. The inventor now provides a new sequencing method in which beads tethered to a solid support are used as labels in sequencing reactions. The probes or bases which bind to the polynucleotide to be sequenced during the sequencing methods are all provided on the bead.

Such a method has various advantages as the probes/beads are provided locally. The beads and probes/bases may be reused and do not need to be added into the reaction as they are present locally. The bead binding to the polynucleotide to be sequenced and release from the polynucleotide may be readily controlled via fluid flow or other external forces, e.g. an applied magnetic field. Furthermore, low costs can be envisaged due to the use of a small contained reaction system with no probe or bead loss. Rapid binding and high accuracy is also achievable.

The basis of the method is shown in FIG. 1. The signal generated by the bead is different when the bead is in the bound (to the tether and polynucleotide) or unbound (tether-only) position. When the bead binds to the polynucleotide via the intermediacy of the probes carried on the bead, the bead is brought into closer proximity to the pixel, thus creating a change in the signal, in this case, a shadow and a reduced light signal. When the probe (or a part or linker thereof) is released by cleavage of a cleavage-sensitive portion or linker, the bead is released to its original position and the signal changes, e.g. light reaching the pixel increases. Determining which probe (or base) has bound to the target polynucleotide is achieved by using probes which can be differentially identified by different cleavage means as described hereinafter.

Thus in a first aspect the present invention provides a method for determining a nucleotide sequence of a single polynucleotide,
wherein:
a) said polynucleotide is immobilised on a solid support;
b) said solid support comprises a surface with one or more sensory elements;
c) a bead is attached to said solid support by a tether;
d) a set of probes or a set of bases is attached to said bead,
wherein each base or probe is optionally attached to said bead via a linker,
wherein said set of probes or set of bases comprises at least one complementary probe or base for each possible permutation of the one or more bases to be sequenced in each cycle of said method,
wherein said complementary probe comprises at least a portion which may be complementary to a region of said polynucleotide comprising said one or more bases to be sequenced,
wherein each at least one complementary probe or base contains a cleavage-sensitive portion or is attached to said bead via a cleavage-sensitive linker and the cleavage-sensitive portion or linker in the at least one complementary probe or base for each of the different possible permutations is different and can be cleaved by a cleavage means specific to said cleavage-sensitive portion or linker;
and wherein said method comprises the steps of:
(i) contacting said polynucleotide with said bead such that the complementary base which is complementary to said one base to be sequenced or the complementary probe which comprises at least a portion which is complementary to said region comprising said one or more bases to be sequenced binds covalently to said base or said region comprising said one or more bases in said polynucleotide, wherein binding of said bead alters the signal at said one or more sensory elements;
(ii) sequentially applying each of the cleavage means specific to each different cleavage-sensitive portion or linker until said bead is released from said polynucleotide to identify which complementary base or probe bound to said polynucleotide to determine said one or more bases to be sequenced;
(iii) optionally, when a set of probes is used, restoring the probe which bound to said polynucleotide to its original pre-polynucleotide binding form;
(iv) optionally, modifying said polynucleotide to reveal the next base or more than one base for sequencing; and
(v) repeating each cycle of steps (i) to (iv) one or more times and in each cycle one or more bases of said sequence are identified.

In a preferred aspect, steps (i) to (iv) are repeated more than once, i.e. more than one cycle is performed, preferably at least 2 cycles as discussed hereinafter.

Hence, the method of the invention determines whether a base or probe has been incorporated into a polynucleotide to be sequenced by assessing which cleavage means is required to release the bead from the solid support and thus which base or probe bound and hence the sequence to which it bound in the polynucleotide can be identified.

The term "determining a nucleotide sequence" as used herein refers to the determination of a partial as well as a full sequence. (This phraseology is used interchangeably with "identifying" a base or bases in a sequence.) Any sequence length is encompassed by the determination of a nucleotide sequence, hence, at least one nucleotide base may be determined by the method, although preferably more than one nucleotide may be determined e.g. at least 2, 3, 10, 20, 30, 40, 50, 60, 70, 80, 90, 100, 200, 300, 400, 500, 600, 700, 800, 900, 1000, 2000, 4000, 6000 or 10000 or more nucleotides may be determined. Thus, preferably the steps of the method, (i.e. each cycle) are performed at least 2, 3, 10, 20, 30, 40, 50, 60, 70, 80, 90, 100, 200, 300, 400, 500, 600, 700, 800, 900, 1000, 2000, 4000, 6000 or 10000 times or proportionally lower if multiple bases are determined in each reiterative cycle.

Determination of the nucleotide sequence includes the identification of the specific base at a particular position (i.e. A, T/U, G or C), i.e. absolute identification, or provides partial identification of that base, e.g. the method may identify a set of bases, of less than 4, (i.e. 3 or 2) which consists of the options for that base, e.g. A or T, but not G or C, or A, T or G but not C. Alternatively the partial identification provides information on the identity of the base which when coupled with information obtained, e.g. in other cycles, allows absolute identification of the base. Such partial identification in a cycle is especially useful when more than one base is to be identified (i.e. read) in each cycle, i.e. when the number of probe bases contacting the target which are not fully degenerate in the probe sets is two or more. The partial identification which is obtained may be especially useful if the "step size", i.e. the number of bases progressed in each cycle is less than the number of bases involved in the reading (e.g. two bases are identified per cycle, but the target sequence progresses, e.g. is shortened, only one base at a time, for example in stepwise ligation in which cleavage may remove a single base from the target sequence before the next cycle). A combination of the information obtained from overlapping readings may be used to obtain the sequence unambiguously or close enough to unambiguously to be useful, especially when the individual that is the source of the sequencing material belongs to a species for which the genome mapping is known, and primarily single nucleotide polymorphisms (SNP) data is the aim of the sequencing. The fact that each base will be involved in at least two reading cycles may, with the right combination of probe sequences in the probe sets, be used to enhance the information level to increase the data quality, e.g. to identify the base in instances for which the ligase has the lowest selectivity with higher certainty without the need for a high number of probe sub-sets.

Thus, by way of example, for two bases identified in each cycle, but one base step size, 4 probe sub-sets (with one sub-set for each permutation as described hereinafter) can be used instead of 16, and still the base sequence may be identified with higher quality of SNP data, in nearly all cases when the genome map is known. In this case, in each of the probe sets 4 different types of probes (4 sub-sets) are present though not distinguished. Thus in the first cycle it can be established that the target two base sequence has 4 possibilities based on the probe sub-set which contains the probe that binds. In the next cycle, similarly 4 possibilities can be identified for the target two base sequence. However, in these two cycles the same base is read in both cycles as the sequencing reaction steps forward only one base between cycles. This overlapping information can be combined and improved as sequencing continues to identify the sequence by identifying which of the 4 possibilities that bound is the correct one in light of information revealed in subsequent cycles.

Similarly, when 3 bases are involved in the reading cycles, but only one base step size, e.g. 9 probe sub-sets can be used instead of 64. As all bases in this way have been involved in 3 readings, a single reading fault will in most cases be detected, especially if the genome map is known. In addition double faults may also quite often be detected with the right construction of the probe sets, especially in those cases for which the ligase is least specific, i.e. for T4 DNA ligase the T/G specificity.

Thus, a "cycle" as referred to herein refers to the steps required to achieve binding of a complementary base or probe to the target sequence in which step (i) to (iv) above (or steps (i) to (iii) in sequencing by synthesis methods discussed below) are performed and identification of said base(s) may be partial or complete at the end of that cycle.

Further, "determining a nucleotide sequence" includes resequencing known nucleotide sequences, as well as sequence comparisons and investigating polymorphisms and mutations in known sequences. Additionally, "determining a nucleotide sequence" may encompass determining the positions of one, two or three of the four types of nucleotides in a sequence, for example, it may be desirable to only determine the position of cytosines within a sequence, as well as identifying the positions in the sequence of any or all of the four nucleotide bases.

The "polynucleotide" whose sequence is determined in the method of the invention may be any polynucleotide but is preferably a DNA or RNA sequence.

Typically, RNA sequences are subjected to reverse transcription to produce copy DNA before being subjected to sequencing. Alternatively, if an RNA sequence is to be used directly in the methods of the invention, reverse transcriptase/RNA polymerase or RNA ligase may be used to incorporate the complementary base or the probe as discussed further below, rather than DNA polymerase or DNA ligase which would be employed for a DNA sequence. The polynucleotide sequence may further be any length but comprises at least two nucleotide bases and generally at least 3, 4, 5, 6, 7, 8, 9, or 10 nucleotide bases. For example, polynucleotide sequences of at least 100, 200, 300, 400, 500, 600, 700, 800, 900, 1000, 2000, 4000, 6000 or 10000 bases may be examined using the present invention. The polynucleotide may include additional end sequences e.g. adapters which have been attached to aid binding to the solid support.

As referred to herein, a "single" polynucleotide refers to an individual molecule for sequencing by the method described herein. Where desired more than one molecule may be sequenced simultaneously using the method, but in that case each single polynucleotide's base(s) are identified by bead analysis. The method relies on the use of a bead that produces a signal that is detectable even when only a single bead is present.

As referred to herein, "immobilised" refers to direct or indirect immobilisation to a support, for example, by binding to another molecule, which is bound to the support. Direct immobilisation may be achieved by chemical coupling and indirect immobilisation may be achieved for example by coupling through binding partners, as described hereinafter, e.g. by hybridisation to a complementary oligonucleotide, e.g. through linking molecules. This form of indirect coupling is preferred.

Hybridisation may be followed by ligation to avoid release of target polynucleotide at elevated temperatures or applied forces, especially if the region of hybridisation is short.

The "solid support" may be any solid support, for example a slide e.g. a glass slide, microarray, microparticle etc but particularly may be an apparatus for detecting the bead as described further below e.g. as identified in WO2010/109159, WO12/042052 or WO12/042043, which are hereby incorporated by reference (i.e. a chip for optical detection, and this may be modified appropriately for other forms of detection e.g. for magnetic detection). Where necessary, the solid support, e.g. chip, may be modified to allow appropriate binding of target polynucleotides, e.g. to allow binding at specific sites to allow performance of the method and detection of the beads.

As discussed above, the complementary base or the probe is bound to the polynucleotide whose sequence is to be determined (target sequence). Hence, preferably, the polynucleotide sequence of the invention may be at least partially single stranded to allow the binding of the complementary base or probe. Particularly, the polynucleotide sequence may be single stranded with a complementary oligonucleotide sequence attached 5' to the polynucleotide portion whose sequence is to be determined, providing a primed polynucleotide sequence which can be extended e.g. by the incorporation of complementary bases by polymerisation. Alternatively, the polynucleotide may be mostly double stranded, for example, double stranded with a single stranded protrusion or portion of a few nucleotide bases, e.g. 2, 3, 4, 5, 6, 7, 8, 9, 10 or more nucleotide bases to which a probe may bind e.g. by ligation, e.g. a complementary double stranded probe with a complementary overlap. As discussed below, probes may be single stranded or may be double stranded with single stranded protrusions which may bind to a part or all of the single stranded protrusion in the polynucleotide sequence.

The term "bead" as used herein refers to a microparticle which is typically but not necessarily a spherical solid support. Although the size of the beads is not critical, they may for example be of the order of diameter of at least 0.05, 0.1, 0.3, 0.5, 1, 1.5, 2, 2.5, 3 or 3.5 µm and have a maximum diameter of not more than 50, 20, 10, 8 or 6 µm. Particularly, beads of 1 or 2.8 or 4.5 or 10 µm may be used in the invention. By diameter is meant size along the longest axis of the bead or along any axis of a spherical bead. "Radius" denotes half of this diameter. Preferably the radius of the bead is larger than the length of the polynucleotide to be sequenced at the start of the sequencing reaction.

In methods described herein for each single polynucleotide only a single probe/base (attached to the bead) will bind in each cycle. Reference to "beads" in the plural should be read in the singular or reflects multiple reactions being conducted together but each on a single polynucleotide.

Monodisperse beads, that is those which are substantially uniform in size (e.g. size having a diameter standard deviation of less than 5%) may be used in the present invention as they provide very uniform reproducibility of reaction.

The bead can be made from any material which allows the formation of a suitable solid support. Non-magnetic polymer beads suitable for use in the methods of the invention are available from Life Technologies/Thermo Fisher Scientific (e.g. Dynabeads®) as well as from Qiagen, Serotec, Merck, Promega, to name a few. Non-magnetic beads may be manufactured from many different materials well known in the art, for example, from plastic e.g. from polystyrene.

However, to aid manipulation and separation, magnetic beads are preferred. The term "magnetic" as used herein means that the bead is capable of having a magnetic moment imparted to it when placed in a magnetic field and thus is displaceable under the action of that field. In other words, magnetic beads may readily be moved by the application of a magnetic field which provides a quick, simple and efficient way of manipulating the position of beads before and after the method steps described herein.

Thus, the magnetic particles may be moved by, or maintained under a magnetic field e.g. using a permanent magnet.

Magnetic beads comprise magnetically responsive material which responds to a magnetic field, for example, paramagnetic materials, ferromagnetic materials, ferrimagnetic materials and metamagnetic materials. Hence, iron, nickel and cobalt as well as metal oxides such as $Fe_3O_4$, $BaFe_{12}O_{19}$, CoO, NiO, $Mn_2O_3$, $Cr_2O_3$ and CoMnP can be used. The magnetically responsive material may be only one component of the bead, whose remainder may consist of a polymeric material to which the magnetically responsive material is affixed.

The quantity of magnetically responsive material in the bead is not critical and can vary over a wide range, for example, from about 1% to about 75% by weight of the particle as a whole. The range may be from 2% to 50%, from 3% to 25% or from 5% to 15%. The magnetically responsive material can be dispersed throughout the polymer, applied as a coating on the polymer surface or incorporated or fixed in any other manner that secures the magnetically responsive material to the polymer. Hence, the magnetically responsive material may form the nucleus or core of the bead.

The polymeric material that forms the remainder of the bead can be any material that can be formed into a solid bead. Examples of suitable polymers are polyesters, polyethers, polyolefins, polyalkylene oxides, polyamides, polyurethanes, polysaccharides, celluloses and polyisoprenes. Crosslinking is useful in many polymers for imparting structural integrity and rigidity to the bead.

Superparamagnetic beads, for example those described by Sintef in EP-A-106873, can also be used which allow the avoidance of magnetic aggregation and clumping of the beads (in preparing the apparatus for the method of sequencing) even with high permeability. Further the magnetic particles sold by Invitrogen as Dynabeads are particularly suited to use in the present invention.

A particular advantage of using magnetic beads is that the beads can be "pulled down" onto the polynucleotide which is immobilised on the solid support, to enable binding of the bead associated bases or probes to the polynucleotide or alternatively "pulled away" from the polynucleotide to the limit of the tether (i.e. under tension) to allow signal assessment.

The bead may be attached to each of the bases or probes either directly or indirectly in any convenient way, according to techniques well known in the art and described in the literature but ensuring that the bead does not prevent access of the probe or base to which it is attached to the target polynucleotide or prevent required reactions taking place, e.g. polymerisation, ligation or cleavage reactions.

Thus, the base or probe may be attached directly to the beads. Such attachment may readily be achieved by methods (e.g. coupling chemistries) well known in the art and conveniently, the base or probe may be bound directly to the bead for example by coating. For example, carboxyl-activated beads may be used and the base/probe and/or tether may be attached through appropriate amino groups.

Alternatively, the bead may be indirectly attached to the test complementary base or probe. The base or probe may therefore be attached to the bead through one or more other molecules which may be directly attached to the bead. These may give rise to a covalent or non-covalent association. Preferably the association is covalent. In a preferred aspect, the bead may carry one or more linking moieties or spacers which have an affinity for the base or probe or for a tag incorporated into the base or probe. Preferably this indirect binding is achieved via binding partners. In this case, the bead may conveniently carry or be provided with a binding moiety capable of binding to the base or probe such that binding occurs via at least two binding partners of a binding pair. As referred to herein a "binding pair" refers to a pair of molecules which form a specific and stable interaction. Examples included DNA:DNA, ligand:receptor, antibody:antigen interactions. Such binding moieties are well known in the art e.g. biotin/streptavidin may be used where the base or probe is coupled to a biotin group and the beads are streptavidin coated. In a preferred embodiment the binding is through DNA:DNA, e.g. use of polyT oligomers on the bead to which polyT tails of the probes are attached.

In a preferred aspect the base or probe may be attached to the bead by biotin/streptavidin binding or by biotin/avidin binding in which biotin and streptavidin form the binding partners. Hence, streptavidin or avidin coated beads may be used to bind a base or probe which is linked to a biotin group. Other binding pairs which may be used include digoxigenin:antidigoxigenin.

In a particularly preferred aspect, the base or probe is attached to said bead via a linkage (preferably, but not necessarily, including binding pairs), which is cleavable. In this case the linker may form the cleavage-sensitive linker described herein. This allows release of said bead after its binding to the polynucleotide to be sequenced via the probe or base on the bead. In a further preferred aspect said cleavable linkage has a restriction site recognized by a restriction enzyme and optionally also the cleavage site which may be within the restriction recognition site (also referred to herein as the restriction site or recognition site) or outside the recognition site. Conveniently this may be generated by use of at least partially single stranded oligonucleotides which are binding partners which together form a recognition site and cleavage site once hybridized.

The set of bases or probes are attached to the bead prior to binding to the polynucleotide. Single or preferably multiple copies of each unique base or probe are attached onto each bead. Preferably said bead carries at least 100, 500, 1000, 10000 or 100000 probes or bases and carries all the sub-sets of probes or bases required for each possible permutation (as described hereinafter) of the one or more bases to be sequenced. Probes or bases of each sub-set are distinguishable from one another by virtue of their cleavage-sensitive portion or linker, as described hereinafter.

The "tether" as referred to herein is a molecule which binds both the bead and solid support. Optionally the tether may also attach to the polynucleotide to be sequenced. The tether is preferably of sufficient length to allow the bead a higher degree of freedom until it is bound to the target sequence via the intermediacy of a probe or base attached to the bead. Thus preferably the tether is longer than the target polynucleotide (or at least the length of the tether from its point of attachment to the solid support to the bead, is longer than the length of the target polynucleotide from its point of attachment to the solid support to the terminal end of the polynucleotide to which the probe/base may bind). Depending on the sequencing method used, the length of the polynucleotide to be sequenced may alter during sequencing, e.g. may lengthen or shorten during the process. The tether should preferably be longer than the longest anticipated length of the target polynucleotide during sequencing. The differential between these lengths allows the bead to adopt a different position when bound only by the tether or when bound also to the polynucleotide for sequencing. Alternatively however, the tether is not necessarily longer than the polynucleotide and in that case may be attached to the solid support at such a position that the bead when under tension is at a different position when in the tether-only compared to the polynucleotide-bound position. When the bead is bound to the polynucleotide the bead is subject to a restriction of freedom due to either the shorter length of the target:probe combination compared to the length of the tether or due to the positioning of the tether compared to the target polynucleotide, resulting in a shorter distance and/or a different positioning in relation to some reference position, i.e. the detection point which in the present case is the sensory elements.

Preferably the tether is bound covalently to the bead and/or solid support.

The tether is preferably a linear organic molecule such as a polynucleotide or polypeptide. Preferably the tether is a polynucleotide, wherein preferably the polynucleotide is 1000 to 3000 nucleotides in length. In an alternative preferred embodiment the tether may be a polypeptide particularly a polypeptide with elastic properties to aid movement of the bead towards the target polynucleotide when its movement is not restricted by external forces such as fluid flow or magnetism.

The bead may carry a single tether or optionally additional tethers may be provided which may be the same or different.

The term "base" or "nucleotide" as used (interchangeably) herein includes the natural nucleotides of adenine, guanine, cytosine, thymine and uracil, particularly in the 2'-deoxy form or non-natural nucleotides which function in the same way, i.e. form a complementary base pair with a natural nucleotide and can be incorporated into a polynucleotide sequence by polymerisation or ligation.

A "set of probes" as referred to herein is a plurality of probes comprising probes for each possible permutation of the one or more bases to be sequenced in each cycle. A "set of bases" as referred to herein is a plurality of bases comprising bases for each possible permutation of the base to be sequenced in each cycle.

"Each possible permutation" of the one or more bases to be sequenced refers to the possible permutations that may be generated by presenting one of the possible bases at each of the positions of the bases to be sequenced. It should be noted that in the case of partial rather than absolute sequence identification, the "possible base" may have more than one identity in the molecule to be sequenced. Thus, for example if the sequencing allows only the determination of e.g. (i) A or T, or (ii) C or G, the "possible base" is A/T or C/T and these are the possible permutations of the bases to be sequenced. Nevertheless, to allow the probe to bind to the molecule to be sequenced, probes must be provided which will bind to either alternative, but in that case each of these probes (which form a sub-set as described herein) are identified by the same cleavage means, i.e. can not be discriminated from one another.

In the case of absolute sequence identification, each possible permutation reflects the full set of base permutations possible in the molecule to be sequenced. Thus, in this case, when only one base is to be sequenced there are 4 possible permutations. When two bases are to be sequenced there are 16 possible permutations (4 possible bases at each position) and so on.

Probes or bases for each permutation are referred to herein as a sub-set (which together make the set of probes or bases). Thus, in the event that only one base is to be sequenced, for absolute sequencing, 4 sub-sets of probes or bases are provided, namely a sub-set in which a C is present for binding to a complementary G in the polynucleotide sequence, and similarly a G, T and A sub-set. (If partial sequencing is undertaken, fewer than 4 sub-sets may be provided.) If two bases are to be sequenced (absolutely) in each round, then 16 sub-sets of probes or bases are provided, i.e. a AA, AT, AG, AC, CA, CT, CG, CC, GA, GT, GG, GC, TA, TT, TG and TC sub-set. Similarly if three or four bases are to be sequenced in each round, 64 or 256 sub-sets of probes or bases are required for each cycle. The probe or base sets and sub-sets required in each cycle may be the same or different depending on the length of the probe, the region of complementarity and the size of the sub-sets of probes.

Within each sub-set of probes a plurality of probes may be provided which provide complementarity to a region of the polynucleotide to which the probe may bind, which is not the one or more bases to be sequenced, i.e. to allow binding of the probe to an unknown target sequence. When the sequence is unknown, degenerate or wobble bases may be used in these positions leading to an array of probes, one of which will be able to bind to the polynucleotide.

Thus, by way of example, if a single base is to be determined in each round, but the probe has an overlap of 4 bases which may bind to the polynucleotide, the following probes may be provided:

Sub-set 1: overlapping region: ANNN (i.e. 64 probes)
Sub-set 2: overlapping region: CNNN
Sub-set 3: overlapping region: TNNN
Sub-set 4: overlapping region: GNNN In this scenario, 4 probe sub-sets are provided which together contain a total of 256 probes. Multiple copies of each unique probe are preferably provided on the bead.

(Similarly multiple copies of each of the 4 bases are provided on beads as the set of bases.)

Thus, preferably the number of bases in the probe (or the single-stranded portion of the probe) are higher than the number of bases read (i.e. the number of bases whose identity is determined), e.g. a probe of 5 bases may be used in a cycle in which only the identity of the first base is determined. When the probe (or single-stranded portion thereof) is longer than the number of bases to be sequenced in each cycle, to allow binding to the target polynucleotide sequence, variation in the bases which are not complementary to bases to be sequenced is required. Thus degenerate or wobble bases may be used at these positions. Thus for example, if only a single base is to be determined, but the probes (or the single stranded portion of the probes) are 6 bases in length, degenerate or wobble bases should be used in 5 base positions. In this case there are 4 permutations which are possible for absolute sequence determination but a sub-set of probes covering degenerate bases is required for each permutation. Thus, in this case, the 4 subs-sets would comprise ANNNN, TNNNN, CNNNN and GNNNN in which each of these sub-sets would contain 4×4×4×4=256 different probes. This provides sets of probes degenerate in the positions not being read. In this case, as used with the sequencing by ligation method, the readout from the method will be the base present at every fifth position. To identify the intervening 4 bases, the reaction may be repeated by releasing the synthesised strand and restarting the process at another start point, such that the sequence is conducted 5 times in total to provide the full sequence. When used with the stepwise ligation and cleavage method the reading will progress one or more bases in each cycle depending on the reach of the cleavage enzyme.

Each sub-set of probes and bases for the different permutations are present on the same bead, and each sub-set can be distinguished from one another by virtue of the cleavage-sensitive portion or linker specific to that sub-set of probes or bases, e.g. the probes or bases of the different sub-sets have a different release mechanism which alters the signal associated with the bead, e.g. a specific recognition/cleavage site which is part of the probe or which attaches the bead to the probe or base.

The base or probe bound to the polynucleotide may have a terminating effect preventing further extension or incorporation of other bases or probes into the sequence. The use of a dideoxynucleotide is not appropriate as introduction of this nucleotide leads to a permanent termination. Therefore, for terminations during the sequence reaction and preceding the final cycle, alternative known reversible modifications may be used. In this case, once the incorporated base or probe has been detected by virtue of alteration of the bead's signal before and after cleavage, the terminating effect can be chemically neutralised, allowing further incorporation or binding of a base or probe to the polynucleotide sequence. Terminations of this sort are known in the art, e.g. modifications to the 3' OH group such as in Jingyue et al. US 2004/0185466, FIG. 14. These terminating groups may be cleaved at the end of the cycle to allow continued polymerisation (see Jingyue et al: WO02/79519 which refers to suitable reagents for doing so). In the case of probes which are used for, e.g. ligation methods, these probes essentially terminate the reaction (e.g. until the cleavage reaction takes place in the case of ligation cleavage methods or through use of probes to specific sequences) and thus no terminating nucleotides are required on said probes though terminating bases may be used, e.g. in which the 5' is dephosphorylated. This may be reintroduced for the next cycle by use of an appropriate kinase.

The terminating effect of the probe may be removed by cleavage of the labelled probe, for example in a method involving stepwise ligation and cleavage steps, by a nuclease (e.g. a restriction enzyme such as a nuclease or RNA endonuclease).

Assessing whether a probe or base carried on the bead has bound to the polynucleotide may be performed at various points during the method, as described hereinafter, particularly, before and/or after any use of the various cleavage means as described hereinafter.

As used herein a "complementary base" refers to a base which specifically base pairs with a base to be identified in the polynucleotide. Thus, an incorporated complementary base will be an adenine if the base to be identified in the polynucleotide is a thymine or will be a guanine if the base to be identified in the polynucleotide is a cytosine and vice versa.

As used herein a "complementary probe" refers to a probe which specifically base pairs with one or more bases to be identified in the polynucleotide. Thus the complementary probe comprises at least a portion which is complementary to a region of the polynucleotide which comprises (or consists of) the one or more bases to be sequenced. The probe may be complementary along its full length to a region of the target polynucleotide or may only contain a region which is complementary to a region of the target polynucleotide containing the one or more bases to be sequenced.

The "portion" of the probe "which may be complementary to a region of said polynucleotide comprising said one or more bases to be sequenced" refers to a sequence of one or more nucleotides or bases which is capable of binding to the target polynucleotide region when they are complementary.

The "region" of the polynucleotide may consist of the one or more bases to be sequenced or may be a longer stretch of consecutive bases containing those bases.

As referred to herein the "at least one complementary probe" for each permutation is a probe for each of the possible permutations of the base(s) to be sequenced. Where more than one such probe is present, this may be another copy of the same probe or probes with degenerate bases which allow binding to bases of the polynucleotide which are not bases to be sequenced, as described above.

Thus, the complementary base or probe refers to a probe or base which may exhibit the desired complementarity to the target sequence. As described above, a limited number of permutations are possible, for example for a single base only 4 permutations (or less for partial sequencing) are possible. The bases or probes on the bead are used to present the different permutations to establish if the base or probe has complementarity to the target sequence and hence will bind to that sequence. Bases or probes without the desired complementarity will not bind to the target sequence but are referred to as complementary probes or bases in view of their potential to bind a polynucleotide depending on its sequence. The probes and bases on the beads may also be considered test probes and bases.

As discussed in more detail hereinafter, each sub-set of probes has an associated, common, cleavage-sensitive portion within it or linker attaching it to the bead. Each sub-set of bases is attached to the bead by a different cleavage-sensitive linker. The identification of which base or probe (or sub-set of bases/probes) has bound to the target polynucleotide may be achieved by selective cleavage using a cleavage means specific to a sub-set of probes or bases. Alternatively, partial information on the identity of the probe may be obtained which may be coupled with information obtained in later cycles as discussed hereinbefore.

The probe may comprise at least 2, 3, 4, 5, 6, 7, 8, 9, 10, 15, 20, 25, 30, 40 or 50 nucleotides (preferably less than 50 or 100 nucleotides). In the event that the probe is double stranded, each strand may comprise this number of nucleotides.

The probe may be single stranded or may be at least partially double stranded, depending on the specific method in which it is to be used. As described below, probes for use in sequencing by ligation methods may be single stranded, whereas probes for use in sequencing by stepwise ligation and cleavage methods may be at least partially double stranded. In this aspect, the probe may be double stranded with a protruding single stranded portion, for example of at least 1, 2, 3, 4, 5 or 6 nucleotide bases, which may be complementary to all or part of a protruding single stranded portion of a polynucleotide sequence. Thus, it is not critical whether the protruding strand of the probe is a 5' or 3' end, as long as it is capable of ligating to the protruding strand of the polynucleotide. Preferably, the protruding strands of the polynucleotide and the probe form a perfectly matched duplex. The probe may further, preferably, comprise a nuclease recognition site for a nuclease (restriction enzyme) which allows nuclease cleavage at a position remote to the recognition site. This recognition site may constitute the cleavage-sensitive portion of a probe which may be cleaved in a cleavage step of the method of the invention. As used herein reference to the cleavage-sensitive linker or portion which "can be cleaved" encompasses a linker or portion which facilitates or allows cleavage but that cleavage occurs outside that linker or portion. Thus, in this case the recognition site may be the cleavage-sensitive portion and cleavage may occur within or outside that cleavage-sensitive portion.

Alternatively or additionally, the recognition site may be used in stepwise cleavage and ligation reactions discussed hereinafter. Preferably the nuclease is a type IIb restriction enzyme, preferably AloI, ArsI, BaeI, BarI, BpiI, Bsp24I, FalI, Hin4I, NmeDI, PpiI, PsrI or TstI, or a type IIs restriction enzyme, preferably AarI, Acc36I, AceIII, BbsI, BfuAI, BtgZI, Eco31I, EcoO441, EspI, FokI or LweI. When such a nuclease forms the cleavage means of the invention, multiple different cleavage means are required for each permutation. Thus, for example 4 different cleavage means may be required, each specific for a different cleavage-sensitive linker or portion. In that case 4 different nucleases with different recognition sites but preferably a common reach are selected. To achieve the required specificity, conditions and enzymes which result in altered or relaxed specificity ("star" activity) should be avoided. To avoid cleavage of the target by the nucleases, the target may be methylated. To enhance specificity, methylation enzymes specific to the restriction enzymes to be used may be employed. Such methylation enzymes, which occur naturally for each restriction enzyme, methylate target sequences to avoid cleavage by that restriction enzyme. Thus, restriction enzymes for which the corresponding methylation enzymes have been isolated and which are commercially available (or which could be readily obtained) are preferred. (Nevertheless, it will be appreciated that selection of enzymes, such as restriction enzymes, is principally guided by the specificity of those enzymes for particular recognition and cleavage sites in accordance with the requirements of the methods of the invention.) In the alternative more general methods of protection of the target may be employed.

The nuclease recognition site may allow cleavage by a nuclease at least 1, 2, 3, 4, 5, 6, 7, 10, 15 or 20 bases up- and/or down-stream from the nuclease recognition site. This may be considered the "reach" of the cleavage enzyme. In methods described hereinafter, preferably said nuclease generates a long overhang (single-stranded region) on cleavage for the next cycle. In this regard, the nuclease may be a type IIb restriction enzyme which on cleavage yields a 5-bp overhang. Alternatively, a type IIs restriction enzyme which on cleavage yields a 1, 2, 3 or 4-bp overhang may be used.

Preferably the nuclease recognition site is the cleavage-sensitive portion referred to herein. This cleavage-sensitive portion may optionally also contain the cleavage site or the cleavage site may be outside the cleavage-sensitive portion.

As discussed above, a probe of one of the set of probes covering all permutations in the target sequence is complementary (or has a portion or region which is complementary) to one or more bases in the polynucleotide. Thus, the probe should be capable of being ligated to the polynucleotide to allow its incorporation therein. Identification of one or more bases in the polynucleotide may then be possible. The portion of the relevant test complementary probe which is complementary to the one or more bases is found within the single stranded part of any probe i.e. the part which can ligate to the polynucleotide. In a partially double stranded probe, the complementary portion is found in the single stranded protrusion. Preferably, the single stranded portion of the probe will have 100% complementarity with a corresponding region in the polynucleotide, although this is not necessary. For example, in embodiments where only a single nucleotide is to be identified with a probe, perfect base pairing is only necessary for identifying that particular nucleotide. Typically, in such cases, the terminal nucleotide of the test probe which is incorporated, e.g. ligated to the polynucleotide, will be complementary to the base to be identified in the polynucleotide, though the complementary nucleotide may not be at the terminal end of the probe.

If more than one nucleotide is to be identified in the polynucleotide in each cycle, at least 2, 3, 4, 5, 6 etc nucleotides of the probe which successfully ligates with the polynucleotide will be complementary to those in the polynucleotide. As discussed herein, in such a case it will be necessary to produce sufficient probes to cover each permutation.

Each of the sub-sets of probes may be tested for successful ligation with the polynucleotide in order to allow identification of the probe which ligates and thus the sequence of the target nucleotide in the polynucleotide.

Therefore, although in a preferred embodiment, the single stranded parts of the probes which will successfully ligate to the polynucleotide may be 100% complementary thereto, it is possible that the single stranded portions of the probes only share at least 80, 90 or 95% complementarity thereto.

A "linker" as referred to herein is one or more molecules which facilitate the binding between the bead and each base or probe. A linker may be used to allow spatial separation from the bead and hence free binding to the polynucleotide and/or may be used to provide a functionality, e.g. a cleavage-sensitive linker. The attachment may be covalent or non-covalent. The linker may be formed of a binding pair as referred to hereinbefore, e.g. a DNA:DNA linker. Preferably the linker is a polynucleotide linker which is preferably double-stranded.

The "cleavage-sensitive portion" is a portion of the probe which is sensitive to cleavage by a cleavage means. This extends to a portion of the probe which facilitates cleavage of the probe or facilitates cleavage of an adjacent, attached, polynucleotide sequence. Thus for example the probe may comprise a recognition site for a nuclease, but the nuclease may cleave at a site outside the probe (e.g. in the polynucleotide sequence once the probe is bound to that polynucleotide sequence). The recognition site in this instance is referred to as the cleavage-sensitive portion.

The "cleavage-sensitive linker" is a linker which is sensitive to cleavage by a cleavage means. This extends to a linker which facilitates cleavage of the linker or an adjacent, attached, molecule. Thus for example if the linker is a polynucleotide it may comprise a recognition site for a nuclease, but the nuclease may cleave at a site outside the linker (e.g. in the attached probe sequence). The recognition site in this instance is referred to as the cleavage-sensitive linker.

The "cleavage means" as referred to herein is a means of achieving cleavage of a cleavage-sensitive linker or portion under the appropriate conditions. As noted above, depending on the number of bases to be read in each round of sequencing, a minimum number of different cleavage means are required to allow each different permutation to be distinguished. If absolute sequencing is to be achieved of a single base, then four different cleavage means are required. If two bases are read during each cycle (absolute sequencing) 16 different cleavage means are required, and so on. Appropriate cleavage means include any convenient means e.g. by enzymatic (e.g. using an RNA endonuclease), chemical, photochemical (see WO 2004/007773 and PCT/US2003/021818) means or by light, heat or mechanical means. In order to allow discrimination between different sub-sets of probes more than one cleavage means must be selected. These may be the same type of cleavage means (e.g. enzymatic). Alternatively, a mixture of cleavage means may be used in the method (e.g. chemical, photochemical, heat and mechanical, with one cleavage means specific for one sub-set of probes), particularly where multiple cleavage means of one type would not provide the required specificity. Preferably the cleavage means are enzymes which recognize and cleave the cleavage-sensitive linker or portion. In the case of restriction enzymes, the cleavage-sensitive linker or portion may contain the recognition site which is recognized by the enzyme, but the cleavage site of the enzyme may be within or outside the cleavage-sensitive linker or portion.

Preferably, the cleavage means are enzymes, particularly preferably restriction enzymes as described hereinbefore. Enzymatic cleavage includes nuclease cleavage, for example as part of a method of stepwise ligation and cleavage sequencing. In such methods the cleavage site appears in the target polynucleotide by use of a nuclease which has a cleavage site separate from the recognition site.

Alternatively, as discussed above, the cleavage site may be placed between the base or probe and the bead, e.g. in a linker. Particularly, a restriction enzyme site and optionally also a cleavage site may be incorporated between the bead and the base or probe. Any restriction enzyme may be used and cleavage may then be achieved using any suitable restriction enzyme for that site. Particularly, a type IIs or type IIb restriction endonuclease may be employed as described hereinbefore. The cleavage site may be positioned directly adjacent to the base or probe (i.e. at the part of the probe most proximal to the bead) to enable the cleavage of the bead together with any linker or other binding moiety which may be present or the cleavage site may be positioned directly adjacent to the bead. If the bead labelled probe is incorporated into the polynucleotide by ligation, a nicking restriction enzyme may be used to release the bead.

Cleavage of the cleavage-sensitive linker or portion affords release of the bead from the target polynucleotide such that the bead is attached to the solid support by virtue of the tether only. As discussed hereinbefore, cleavage of the cleavage-sensitive linker or portion extends to cleavage outside the linker or portion in instances in which the recognition site for an enzyme is within the linker or portion, but the cleavage site is outside the linker or portion. Thus, a reference herein to cleave of the cleavage-sensitive linker or portion encompasses not only cleavage of that linker or portion itself but also cleavage allowed or facilitated by that cleavage-sensitive linker or position, e.g. at a cleavage site distant from a recognition site for an enzyme within the linker or portion.

As discussed herein the probe may contain various sequences which provide the required functionality. Thus, the probe may contain:
  i) a sequence comprising a cleavage-sensitive portion;
  ii) a sequence which facilitates restoration of the probe to its original form if the probe is bound to the polynucleotide; and
  iii) a sequence which facilitates removal of at least part of the probe and at least one base of the polynucleotide being sequenced if the probe binds to the polynucleotide.

In each case the sequence providing functionality i) to iii) may be a recognition site for a nuclease, e.g. a nuclease as described herein. Furthermore, sequences i) and ii); or i) and iii) may be the same. Thus, for example the cleavage-sensitive portion may allow cleavage of the attachment between the probe/base and bead and that cleavage may occur at a position which reveals the next base. Similarly, cleavage at the cleavage-sensitive portion may restore the probe to its original form.

"Contacting" as referred to herein refers to bringing the polynucleotide and bead into contact under conditions that allow formation of complementary base pair binding between the polynucleotide and one of the probes or bases carried on the bead if the probe or base has complementary bases to the one or more bases in the polynucleotide, i.e. is a complementary probe or base. This may be achieved by various means, as discussed hereinafter, e.g. magnetic force or liquid flow which may direct the bead away from the polynucleotide when binding is not desired, may be removed.

Covalent binding may be achieved by any method or technique which allows the binding of a complementary base or probe to its complementary sequence in the polynucleotide sequence. In a preferred embodiment, the covalent binding of the base or probe is achieved by polymerisation or by ligation. Particularly, a single base may be incorporated by polymerisation e.g. using DNA or RNA polymerase, or transcriptase/reverse transcriptase, and a probe may be incorporated or bound by ligation. Such incorporation of the base or probe will extend the polynucleotide either in the 5' to 3' or 3' to 5' direction.

"Ligation" as used herein refers to the formation of a covalent bond or linkage between the terminal ends of two or more nucleic acids in a template driven reaction where the ligation may occur enzymatically or chemically. Ligation may be achieved using DNA ligase for DNA sequences and RNA ligase for RNA sequences.

As referred to herein the "signal" of said bead is the signal which is detected by the sensory element. Since the bead moves position during the method and its position indicates whether or not a probe/base has bound to the polynucleotide, a signal may be used which alters on movement of the bead, e.g. position relative to the one or more sensory elements. It should be noted that the length of the target polynucleotide may increase or decrease during the sequencing method, depending on the method of sequencing. This will incrementally affect the position of the bead when bound to the target polynucleotide such that the signal strength or position may vary incrementally during each cycle of the reaction. The discrepancy between the bound and unbound position for the bead may be enhanced by the selection of a sufficiently long tether (for example) and the incremental changes may also be used to monitor the progression of the sequence reaction.

Any method which results in an altered signal on the physical movement of the bead between the bound and the unbound (to the target polynucleotide) form may be used. Preferably the signal is optical activity. Thus, for example incident light may be used and the effect of the bead on the incident light reaching the sensors (i.e. whether or not the bead interferes with the incident light), may be assessed. In an alternative example of optical activity, fluorescence may be the signal and the level of the signal may vary depending on the beads' proximity to the sensors. Alternatively different types of signals may be used such as magnetism (e.g. using paramagnetic beads), surface capacitance or ion currents, in which the level of these signals as assessed by relevant sensors is affected by movement of the bead between the bound and unbound positions.

The "sensory elements" are elements which are sensitive to a variation in a signal. Thus they may be sensitive to alterations in the levels of light, fluorescence, electrical activity, magnetism etc. on, or in proximity to, that sensory element. The sensory element is selected based on the signal to be detected.

Preferably the sensory elements are light-sensitive elements and the signal is measured by assessing the amount of incident light falling on the light-sensitive elements which can be altered depending on the spatial arrangement of the bead relative to the one or more light-sensitive elements which changes as the bead is, respectively, bound to the polynucleotide or removed from the polynucleotide after a cleavage reaction. Preferably the light-sensitive element detects changes in light due to interference, reflection or absorbance of light by the bead.

In the methods of the invention the presence or absence or level of signal associated with the bead is examined to assess whether any alteration in signal occurs during the method. As referred to herein "alteration" of the signal indicates any change in the nature or intensity (either increasing or decreasing) of the signal. Preferably, in methods of the invention on binding to the polynucleotide via the intermediacy of the probes, the position of the bead is modified relative to the position of one or more sensory elements such that passage of incident light is affected. Thus, for example, when not bound to the polynucleotide the bead may be spatially separated from the one or more sensory elements such that incident light is received by the sensory elements leading to a first signal and when the polynucleotide is bound to the polynucleotide the bead's proximity to the one or more sensory elements is altered, e.g. its proximity is increased, thus affecting reception of incident light by the one or more sensory elements and thereby leading to a reduction in the light signal. Since a change in signal occurs when the bead is bound to the polynucleotide or released after cleavage with the correct cleavage means which is associated with a particular sub-set of probes or bases, a change in signal in response to a cleavage means is indicative of the base(s) under investigation.

Thus in a preferred aspect, after said step of contacting said polynucleotide with said bead the presence, absence or level of signal associated with said bead is determined. (The signal associated with the bead before the contacting step may also be assessed to provide a reference signal level for the bead when not bound to the target polynucleotide.) Furthermore after application of each sequential cleavage means the signal associated with the bead may be determined.

As referred to herein a "signal associated with a bead" refers to a signal emanating from a bead or which is modified or affected by the presence of the bead. In the preferred aspect the signal is light and the bead affects the level of light reaching a detector by steric hindrance.

A change in signal after a cleavage step is indicative of successful cleavage and it may then be inferred that the sub-set of probes or bases which carried the corresponding cleavage-specific linker or portion had bound to the polynucleotide. This allows an identification of the probe/base which bound (or at least the relevant sub-set of probes/bases) and hence partial or absolute identification of the one or more bases to be sequenced. Thus an alteration in the signal after a cleavage step is indicative of binding of a complementary base or probe. In a particularly preferred aspect, the level of signal associated with said bead before and after a cleavage step is determined and a decrease of signal after cleavage is indicative of binding of the base or probe containing or linked by the cleavage-sensitive linker or portion to which the cleavage means is specific.

Bead detection may be carried out as described below. Conveniently the method of the invention is carried out on a chip.

In a particular preferred embodiment, the detection of the bead may be carried out using an apparatus comprising a surface which is provided with a means for detecting a bead. The surface may comprise one or more elements which provide an output dependent on the presence, absence or position of a bead. In a preferred embodiment, the detection of the bead may be carried out optically by a method described in WO2010/109159 for example using an apparatus described therein.

In such a method, the polynucleotide may be attached to the surface which is provided with a means for detecting a bead. Thus, the surface may be provided with one or more light sensitive elements wherein each light sensitive element is arranged to detect a bead adjacent thereto. The light sensitive elements may alternatively be replaced or used in conjunction with other elements which are capable of detecting a bead e.g. Hall elements. The one or more light sensitive elements provided on or within the surface are capable of outputting a signal which is dependent on the presence, absence or proximity of a bead and the signal provided from each light sensitive element will therefore indicate whether the bead orientation has changed which implies binding of a base or probe on that bead to the target polynucleotide. In this detection method, the bead is itself directly detected by the one or more light sensitive elements. The bead may be arranged to emit light which can be detected by a light sensitive element e.g. it may be fluorescent, although in a preferred aspect, the bead is detected when it blocks light from reaching the light sensitive element in question. Thus preferably said detection is by detecting light changes resulting from the presence of the bead on a light sensitive surface. Thus, the bead effectively casts a shadow on the element. The light source used may be ambient light or a dedicated light source may be provided. By illuminating the surface, the detection of any shadows created by the presence of beads or the obstruction of light from the light sensitive elements can be detected more easily. Further, to prevent external light sources from affecting results, preferably the light sensitive elements are shielded from external light by a suitable housing.

The light sensitive elements are therefore capable of measuring the amount of light received by the surface, which can determine the presence or absence of a bead. A bead can be detected by an individual light sensitive element or by a group of light sensitive elements, depending on the size of the beads, the light sensitive elements and the distance of the beads from the surface. Hence, it is possible that an individual light sensitive element can detect a bead or that 2, 3, 4, but more likely 4, 9, 16 or more light sensitive elements can detect a bead. The amount of light detected by each light sensitive element and hence the signal output from the light sensitive elements when no beads are present can be used as a reference point against which other measurements can be compared. A reduction in light (i.e. created by the shadow of bead) received by a light sensitive element will result in the output of a signal which differs from that outputted when beads are more distant. As discussed below, the amount of light received by each light sensitive element when a bead is bound to the tether or not will depend upon various factors, including the bead size, the size of each light sensitive element and the length of the polynucleotide attached to the surface.

The "surface" is preferably provided with a plurality of light sensitive elements arranged to form an array. The light sensitive elements may be on or form the outer layer of the surface or may be comprised within the surface e.g. may be present beneath one or more other material layers. Arrays of light sensors or of light sensitive elements are well known in the art and include charged coupled devices e.g. of the type used in cameras or CMOS active pixel sensors. Modifications may be made to such CCD or CMOS image chips as discussed further below. The surface may be the substrate of such a device.

The polynucleotide whose sequence is to be determined may be attached to or placed above the one or more light sensitive elements present in or on the surface to enable the generation of an output from the attached bead. Preferably, a single polynucleotide may be associated with a light sensitive element or a group of elements and may be detected. A polynucleotide sequence may further be divided over more than one light sensitive element or group of elements to enable the sequence to be ascertained more rapidly i.e. for portions of the sequence to be determined by different light sensitive elements, but in each case a single polynucleotide is sequenced.

The bead may cast a shadow on the surface and on a light sensitive element or a group of light sensitive elements when the bead is present (or brought into closer contact with the surface) and hence reduce the amount of light received by the light sensitive element(s). For example, the bead may reduce the amount of light received by the light sensitive element(s) by from about 10-100%, e.g. particularly at least 10, 20, 30, 40, 50, 60, 70, 80, 90 or 95%. It will be appreciated that the output provided will be dependent on the size of bead used, the size of the individual light sensitive elements present on the surface and the length of the tether and the target polynucleotide. Therefore, a bead which is the same size or larger than a light sensitive element may prevent most light from falling on the light sensitive element. Each light sensitive element and bead size combination may be calibrated by measuring the signal output when a bead is in the tether-only position or in the tether and target polynucleotide bound position.

It is possible for a particular bead size to be chosen depending on the size of the light sensitive elements in or on the surface. Preferably, a bead may be selected which corresponds to the size of the one or more light sensitive elements in or on the surface. Hence, a bead may be selected which when attached to the surface will reduce the amount of light by at least 10, 20, 30, 40, 50, 60, 70, 80, 90 or 95%. For example, 1 µm diameter beads may be used in combination with 1.75×1.75 µm light sensitive elements or 2.8 µm diameter beads may be used with 3.2×3.2 µm light sensitive elements.

The light sensitive elements are able to convert the light energy received into voltage which may then be converted into digital data. In this way, the surface comprising the elements is itself capable of detecting the presence of a molecule by detecting a bead attached to that molecule. There is no need for external expensive equipment to be employed to detect the presence of the signal or label attached to the molecule. The surface itself is able to detect the molecule.

As noted above, known CMOS or CCD detectors are suitable for detecting the beads. For example, image chips of the sort used in mobile phones can be used for detecting beads in the method of the invention. Hence the surface of, for example a CMOS or CCD image sensor, may form the surface used in the detection/identification step of the invention.

The CMOS photodetector (or Active Pixel Sensor) has been developed essentially for consumer camera applications e.g. in webcams or mobile phones. Two variants of this detector are available, namely the bare die variant or a variant with the die packaged with a protective glass and bonded to pads that are connected to the external pads made for soldering. The bare die variant may be used directly in the present invention, whereas the packaged die variant CMOS photodetector may be modified by removing the glass lid. For both variants, it may be preferable to remove the layers of microlenses and colour filters which usually cover the pixels because the surface under the lenses and filters is usually a layer of glass, which is preferable, especially to avoid unspecific connection of beads. CMOS or other photodetectors may be manufactured without the additional microlens/filter layers present which are required for use in mobile phones, for direct use in the present invention. Hence, particularly adapted CMOS image chips may be used in the invention.

Particularly, the surface may comprise at least 3 Megapixels (2048×1536 light sensitive elements) or at least 4, 5, 6, 7, 8, 9, 10, 11 or 12 Mpixels. Using standard deposition processes, it may be possible to deposit polynucleotides associated with at least 1, 5, 10, 15, 20, 25, 30, 35 or 37% of the light sensitive elements. The light sensitive elements or pixels present on an image chip are usually the same size, although differences in size may occur. The pixels may be for example in the range of 0.5×0.5 µm to 10×10 µm, for example 1×1 µm, 2×2 µm, 3×3 µm, 4×4 µm, 5×5 µm or 6×6 µm and particularly, the pixels may be 1.75×1.75 µm or 3.2×3.2 µm.

Modifications may additionally be made to the surface e.g. to that of the image chips to assist in the attachment of molecules to the surface. Particularly, the image chips may be coated with gold or may be modified to have silane or antidigoxigenin groups attached. The thickness of the layer of gold which may be used is not critical provided that too much light is not blocked from reaching the light sensitive elements. For example, gold layers may range from 5 to 50 nm. Methods of modifying surfaces in such ways are known in the art. Gold coating may be carried out by vacuum deposition or by deposition from a highly concentrated gold solution. Aminosilane modification of surfaces can be achieved by for example incubating the surface with 5% aminopropyltriethoxysilane (CAS:019-30-2) in dry acetone for one hour at room temperature. Aminosilane surfaces can be used as is, to add desired molecules directly, or can be further modified by adding a bifunctional crosslinker, such as m-maleididibenzoyl-N-hydroxysulfo-succinimide ester in order to be able to bind molecules to the surface. Antidigoxigenin modification is achieved by first priming the surface with a poly-1 lysine solution (10% poly-1 lysine v/v and 10% PBS), and then by adding antidigoxigenin 1:100 in Invitrogen CNB0011 coating buffer A.

Additionally, the surface may be equipped with a flow cell which allows fluid flow to and from the surface. Hence, the flow cell can be used to move the beads within their freedom of movement, e.g. to move the bead away from the surface (to the full extent of the tether) when not bound to the target polynucleotide. The flow cell may also be used to provide ancillary molecules such as unlabeled bases or other molecules required in the sequencing method. Further, the surface may be arranged with a reader which is capable of detecting and reading the signals from each of the sensory elements in or on the surface. The output from each element may be received by a computer. A flow cell may easily be made to contain more than one chip, e.g. it may be produced with 64 image chips. In that case all the chips may be controlled from the same control unit.

The shape of the surface may be additionally or alternatively modified or adapted to assist the positioning of the beads at each position or pixel and to allow a sensitive and accurate method. Hence, the surface may be modified or adapted, for example shaped, to allow the binding of a bead at each position.

Therefore, the surface may be contoured to allow the association or binding of a bead with each sensory (e.g. light sensitive) element. Individual recesses may be associated with or located by each sensory element or groups of sensory elements which allow each bead to attach and to be associated with a single or individual sensory element or group of sensory elements on the surface. The recesses may allow the bead to be positioned only over a single element and to prevent movement of the bead over more than one sensory element or group of sensory elements.

Alternatively, each sensory element or group of sensory elements may be surrounded by a barrier to enable bead attachment and association with only that sensory element or group of sensory elements. Hence, barriers or obstacles may be placed on the surface around the one or more sensory elements.

A combination of recesses and barriers may also be used on a surface. Typically, the sensory elements which will have a polynucleotide attached thereto will be adapted to have a recess or barrier associated therewith. One or more elements on a surface may be adapted, although typically all of the elements may be adapted e.g. to have recesses and/or barriers associated therewith.

The adaptation of the surface in this way e.g. the use of recesses and/or barriers allows a more sensitive and accurate method and may allow longer polynucleotides to be sequenced. Thus, the surface may be adapted to allow the binding of a single bead at each position. Each sensory element or sensory element group and its surrounding barrier or recess may therefore be of a suitable size to bind an individual bead. The sensory element and/or barrier/recess may therefore be adapted to suit any particular bead size used with the surface. The surface may be adapted using techniques well known in the art.

Surface modifications as discussed above may not be necessary during the sequencing method due to the presence of the tether but may assist in the preparation of the apparatus for sequencing.

In addition, to allow connection of target polynucleotides to sensitive areas of the detector (e.g. for light or magnetism) modifications may be necessary. This may be achieved for example by lithographic methods, e.g. defining islands of a gold layer which may connect to a thiol modification at one end of the target anchorage to the surface or by defining islands that are silanized.

Different polynucleotides may be sequenced simultaneously at different positions on the surface. To do so it will be necessary to determine their position on the surface before commencing sequencing. Alternatively, overlapping fragments of a polynucleotide may be generated and placed randomly at separate positions on the surface for sequencing. In this instance, it is not necessary to determine the positions of each fragment on the surface prior to sequencing since the overlapping sequences can be pieced together after sequencing has been completed.

In accordance with the method, the different cleavage means are applied sequentially. Thus a first cleavage means is applied to the system after which the signal associated with the bead is determined. Thereafter a second cleavage means is applied and the signal is then determined. A change in signal indicates that cleavage has occurred, i.e. that the bead has been released from its attachment to the target polynucleotide, e.g. either by cleavage of the linker attaching the bound bead or probe or by cleavage of, or removal of, the probe which has attached to the polynucleotide. This process may be continued until cleavage is achieved. However, in automated processes, each possible cleavage means may be applied and the change in signal recorded after each step. During this cleavage step the bead should be maintained in a fixed position dictated by the length and/or position of its attachment to the solid support, e.g. under the influence of liquid flow or magnetism such that it may adopt only two positions, either attached to the polynucleotide (and the tether) or attached to the tether only. On cleavage the bead should be returned to the tether-only position to avoid the bead contacting the polynucleotide with another probe/base. Thus the bead should be maintained in a state of tension by appropriate means.

As referred to herein the cleavage means may be "applied" by any appropriate techniques compatible with the cleavage means. In cases where the cleavage means is an enzyme this may be applied through the liquid medium supporting the reaction. The cleavage means may also be applied by the appropriate application of e.g. heat or light, as appropriate.

As referred to herein the cleavage means are "specific" to the cleavage-sensitive linker or portion. By this it is meant that the cleavage means is able to achieve cleavage only of the cleavage-sensitive linker or portion to which it is specific (or optionally of a cleavage site outside that linker or portion in the case of a restriction enzyme in which the recognition site but not the cleavage site is present in the cleavage-sensitive linker or portion) and not other cleavage-sensitive linkers or portions of other sub-sets of probes or bases which are used in the method. Thus each "different" cleavage-sensitive portion or linker is paired with a specific cleavage means.

During the cleavage steps the method requires that one identifies which complementary base or probe bound to said polynucleotide to determine said one or more bases to be sequenced. This assessment is made by assessing the presence, absence or level of signal associated with the bead during the step of applying the cleavage means as described hereinbefore.

The assessment of the presence, absence or level of signal associated with the bead may be made at various times during steps (i) and (ii) to allow the determination, e.g. (a) assessment may be made before any binding (i.e. at the start of step (i)), (b) assessment at the end of step (i); and/or (c) assessment of bead signal before and/or after each application of a cleavage means in step (ii). The assessment may be quantitative or qualitative.

The step of determining the one or more bases includes all the actions necessary to achieve the determination, e.g. including the contacting step, the sequential application of cleavage means and assessment of signalling, unless such steps are separately recited. If absolute sequencing is performed, the one or more bases to be sequenced are determined absolutely, i.e. the identity of the one or bases in the polynucleotide are determined unequivocally. However, if partial sequencing is performed, the one or more bases to be sequenced are not determined absolutely, i.e. the identity of the one or more bases in the polynucleotide are not determined unequivocally (e.g. it may be determined that a base is one of two possible bases). Both alternatives are covered by reference to determining the one or more bases to be sequenced.

To achieve the determination of the one or more bases the base or probe which bound must be identified. This information is conveyed by identifying which cleavage means achieved a change of signal. The cleavage means is specific to a sub-set of probes or bases carrying a corresponding cleavage-sensitive linker or portion thus allowing identification of the probe or base (or sub-set of probes/bases) which bound. Since the sequence of the probe or base which bound is known (at least as it relates to the base complementary to the one or more bases to be sequenced) this allows a determination of the one or more bases in the sequence.

Thus, for example the cleavage means may be a specific restriction enzyme and the different sub-sets of probes or bases may include or be attached by corresponding cleavage-sensitive linkers or portions and release of the bead when a specific enzyme is used is indicative of the base under investigation.

In this preferred aspect, the cleavage-sensitive linker or portion comprises a recognition site for a restriction enzyme. The cleavage site for the restriction enzyme may be within or outside the cleavage-sensitive linker or portion.

Thus in a preferred aspect, identifying which complementary base or probe of said set of bases or set of probes bound to said polynucleotide comprises determining the presence, absence or level of signal associated with said bead after each cleavage relative to the presence, absence or level of signal associated with said bead before each cleavage, wherein a change in the signal is indicative of binding of said complementary base or probe with the cleavage-sensitive linkage specific to the cleavage means used in said cleavage step. In a preferred embodiment the level of signal associated with said bead before and after said cleavage step is determined and a decrease of signal after cleavage is indicative of binding of said complementary base or probe with the cleavage-sensitive linkage specific to the cleavage means used in said cleavage step.

Preferably, to improve accuracy, the level of the signal from said bead is detected and may be compared at various time points during the cycle. Conveniently, the signal is detected before and/or after putative binding and/or after release and removal. In a particularly preferred aspect in methods in which the bead (if bound) is removed by cleavage, the signal from the bead is measured before and after said cleavage step and a reduction in said level is indicative of the binding of said bead allowing the identification (in absolute or partial terms) of the target one or more bases by virtue of the probes which attached to said bead. Such methods are useful as enzymatic reactions may be incomplete, e.g. ligation or cleavage, by design or default.

As discussed above, after release of the bead following the cleavage step, the bead should be removed from the polynucleotide by spatially separating the bead from the target polynucleotide to allow discrimination between a target polynucleotide with which a bead is associated after binding of a relevant test base or probe to which said bead was attached and a polynucleotide from which the bead has been released and removed. After release the bead may be moved away from the polynucleotide e.g. by magnets or fluid flow (e.g. over a chip), as discussed hereinbefore.

In accordance with the method of the invention, when probes are used in methods of the invention, the probe that has bound to the target polynucleotide during the method may be restored to its original pre-polynucleotide binding form if necessary. Depending on the probes that are used, after the cleavage step the probe may be retained on the bead but in an altered form. This will in most cases not occur if a cleavage-sensitive linker between the bead and probe is cleaved which generally will remove the probe from the bead in full. However, if cleavage occurs in or is facilitated by a cleavage-sensitive portion in the probe, the probe may be retained on the bead but in a modified form. For example, in the case of stepwise ligation and cleavage an enzyme is selected which cleaves at a site generated by the binding of the probe to the polynucleotide and thus removes both the probe and additional bases from the polynucleotide. In this case the probe that remains on the bead can be restored to its original form by removal of those additional bases. This may be achieved by any appropriate means, but conveniently the probe contains a recognition site for a nuclease which has a cleavage site separate from its recognition site which on cleavage restores the probe to its original form. Thus the recognition site is placed such that the reach of the enzyme is coincident with the end of the original probe. Thus the probe is restored or reverts to its original form, wherein its original form is the form of the probe if it does not bind in a cycle of the method. As the number of accessible probes is generally high, the probability of reusing a probe is low and thus the regeneration may not be necessary or may only be performed in some cycles.

The method of the invention also includes the optional step of modifying the target polypeptide to reveal the next base or more than one base for sequencing. In certain methods of the invention this step will not be necessary if appropriate cleavage means and probes are employed. For example, in the stepwise ligation and cleavage sequencing method, probes are selected with a recognition site which on binding of the relevant enzyme results in cleavage which removes at least part of the ligated probe and at least one base of the polynucleotide being sequenced. In this case no further action to reveal the next base is required (though the probe may need to be restored as described above). However, if the method of sequencing uses different probes or bases, some modification (e.g. truncation) of the polynucleotide may be necessary. In the case of the binding of bases, e.g. in methods of sequencing by synthesis, the bases are attached by a cleavage-sensitive linker and thus no truncation of the polynucleotide is necessary. However, in this case, if any portion of the linker remains this may need to be removed before binding of a base to the next base in the target polynucleotide is possible. Such a modification is encompassed by this step. Thus, the polynucleotide to be modified in this step is the polynucleotide as modified by the preceding steps, i.e. with the probe, base, linker or part thereof attached.

Reference herein to "revealing" the next base(s) is intended to mean that the next base for sequencing is made available for the next cycle. This may be by removing steric hindrance (e.g. a linker (or part thereof) attached to a probe or base), generating a single stranded portion for binding or truncation of the polynucleotide as appropriate. In a preferred aspect of the invention, when a probe is used it contains a recognition site for a nuclease which has a cleavage site separate from its recognition site which on cleavage removes at least part of the complementary probe and at least one base of the polynucleotide being sequenced if that probe binds to said polynucleotide.

As discussed above, the different functionalities discussed above may be provided by one or more sequences in a single probe optionally with its linker. Thus, the cleavage-sensitive portion when cleaved (which incudes cleavage outside the cleavage-sensitive portion when the portion contains only the restriction site for a restriction enzyme) may also reveal the next base for sequencing and/or restore the probe to its original form. Thus said probe optionally together with its linker comprises at least a cleavage-sensitive portion or linker and optionally one or more of:
(i) a recognition site for a nuclease which has a cleavage site separate from its recognition site which on cleavage restores the probe to its original pre-polynucleotide binding form if that probe binds to said polynucleotide during said method; and
(ii) a recognition site for a nuclease which on cleavage removes at least part of the complementary probe and at least one base of the polynucleotide being sequenced if that probe binds to said polynucleotide.

As discussed above the cleavage-sensitive portion in the probe may be (i) or (ii) above.

In the above described method, the steps are performed one or more times and in each cycle one or more bases of said sequence are identified. As mentioned hereinbefore a cycle refers to the steps required to identify one or more bases of the target sequence. As noted hereinbefore, identification of the one or more bases may be absolute or partial.

In one embodiment of the invention, the method of the invention involves the use of a polymerase and sequencing is conducted by synthesis. In this case the method is performed using a base attached via a linker in a set of bases with sub-sets for each permutation (i.e. a sub-set for each possible base, or more than one base in the case of partial sequencing) and a single base is sequenced in each cycle.

Thus, a further aspect of the invention proves a method for determining a nucleotide sequence of a single polynucleotide, wherein:
a) said polynucleotide is immobilised on a solid support;
b) said solid support comprises a surface with one or more sensory elements;
c) a bead is attached to said solid support by a tether;
d) a set of bases is attached to said bead,
   wherein each base is attached to said bead via a linker,
   wherein said set of bases comprises at least one complementary base for each possible permutation of the base to be sequenced in each cycle of said method,
   wherein each at least one base is attached to said bead via a cleavage-sensitive linker and the cleavage-sensitive linker in the at least one complementary base for each of the different possible permutations is different and can be cleaved by a cleavage means specific to said cleavage-sensitive linker;
and wherein said method comprises the steps of:
(i) contacting said polynucleotide with said bead such that the complementary base which is complementary to said base to be sequenced binds covalently to said base, wherein binding of said bead alters the signal at said one or more sensory elements;
(ii) sequentially applying each of the different cleavage means specific to each different cleavage-sensitive linker until said bead is released from said polynucleotide to identify which complementary base bound to said polynucleotide to determine said base to be sequenced;
(iii) optionally, modifying said polynucleotide to reveal the next base for sequencing; and
(iv) repeating each cycle of steps (i) to (iii) one or more times and in each cycle one base of said sequence is identified.

This method also allows the determination of a homopolymer sequence in the polynucleotide. Preferably said method is conducted in the presence of a polymerase such as a DNA or RNA polymerase. Preferably as mentioned above said method involves the use of a base which has been modified to prevent further chain extension and an additional step at the end of said method is preferred where said base is modified to allow further extension, e.g. a protecting group which prevents chain extension is removed.

In this case, the incorporation of a test base and its identity can be determined by virtue of the change of signal during the sequential cleavage steps. Four different cleavage means are required to cleave the cleavage-sensitive linker associated with each specific sub-set of bases for the different possible bases in the target sequence (or less if only partial sequencing is contemplated). The definitions and preferred aspects of this method are as described herein for other methods of the invention.

This method is commonly known as sequencing by synthesis (Jingyue et al., supra). In methods of this sort, linkers and their cleavage sites are preferably selected such that the cleavage point is as close as possible to the base such that polymerization of the next base during the sequencing method is possible.

To avoid stalling, and thereby allowing the reading of long partial sequences, the use of methods not relying on polymerase are preferred. Nevertheless, due to the simplicity and speed of polymerization, particularly when unmodified bases are used, such as in pyrosequencing and Ion Torrent sequencing in which bases are applied one at a time, methods using polymerases may be used and stalling managed by appropriate means such as by use of a modified polymerase and/or appropriate selection of the linker and cleavage point.

Thus, in a further embodiment, the invention encompasses binding one or more probes by ligation to the polynucleotide sequence using preferably a ligase (sequencing by ligation). In this case probes are used which may have a cleavage-sensitive linker or portion.

Preferably said ligation is achieved chemically or enzymatically using a ligase. Suitable ligases for performance of the method include T4 DNA ligase.

In this embodiment, the initial polynucleotide template may be single stranded and its nucleotide sequence may be determined by one or more repeated cycles of duplex extension along the single stranded template. Particularly, the extension may start from a duplex formed between an initialising oligonucleotide and the polynucleotide template where the initialising oligonucleotide is extended in an initial extension reaction by ligation of an oligonucleotide probe to its end to form an extended duplex. The identity of one or more nucleotides in the polynucleotide can be determined by the identifying the probe which bound to the polynucleotide by changes in signal during the cleavage step.

The initialising oligonucleotide used is selected to form a highly stable duplex with the polynucleotide and the length of the initialising oligonucleotide is generally longer than the probes used in the ligation reactions (particularly the length may be 20-30 nucleotides). Further, the initialising oligonucleotide may be G/C rich. The selection of initialising oligonucleotides is described in U.S. Pat. No. 5,750,341.

The probe used in the ligation reaction should be capable of being ligated to the initialising oligonucleotide and should form a duplex with the polynucleotide before the ligation when complementarity exists. Preferably, the probe (or the region thereof which binds to the target polynucleotide) should be perfectly matched to the polynucleotide to allow successful identification of the polynucleotide sequence i.e. the probe should have 100% complementarity to the sequence to be identified. The probes may comprise at least 2 nucleotide bases and particularly may contain 3, 4, 5, 6, 7, 8, 9 or 10 nucleotide bases (preferably less than 10 or 20 nucleotides). To achieve ligation, preferably said probe has a single stranded portion of 3 or more bases, e.g. 4, 5, 6 or 7 bases. In order to identify a particular sequence within the polynucleotide, a sub-set of probes for each permutation should be produced as previously discussed, representative of the total different combinations of bases which are possible within a probe of a particular length. For example, a probe of 2 nucleotide bases may have 16 different combinations of nucleotide bases and hence 16 different probes should be constructed for addition to the polynucleotide sequence (for absolute sequencing). Probe sub-sets may be generated for each permutation if the probe is longer than the number of bases to be detected in each cycle.

In a further and preferred embodiment, the nucleotide sequence of the polynucleotide may be determined by using a method of stepwise ligation and cleavage, such as that described in U.S. Pat. No. 5,714,330 in which the complementary probe is attached to the bead. The method allows the identification of one or more terminal end nucleotides of the polynucleotide sequence and one or more nucleotides are removed from the end of the polynucleotide to allow any further desired cycles of ligation and cleavage to occur.

Thus, in a further preferred aspect the invention provides a method for determining a nucleotide sequence of a single polynucleotide, wherein said method is a method of sequencing by stepwise ligation and cleavage, wherein:
a) said polynucleotide is immobilised on a solid support;
b) said solid support comprises a surface with one or more sensory elements;
c) a bead is attached to said solid support by a tether;
d) a set of probes is attached to said bead,
wherein each probe is optionally attached to said bead via a linker,
wherein said set of probes comprises at least one complementary probe for each possible permutation of the one or more bases to be sequenced in each cycle of said method,
wherein said complementary probe comprises at least a portion which may be complementary to a region of said polynucleotide comprising said one or more bases to be sequenced,
wherein each at least one complementary probe contains a cleavage-sensitive portion or is attached to said bead via a cleavage-sensitive linker and the cleavage-sensitive portion or linker in the at least one complementary probe for each of the different possible permutations is different and can be cleaved by a cleavage means specific to said cleavage-sensitive linker or portion;
and wherein said method comprises the steps of:
(ia) contacting said polynucleotide with said bead such that the complementary probe which comprises at least a portion which is complementary to said region comprising said one or more bases to be sequenced binds covalently to said region comprising said one or more bases in said polynucleotide,
wherein binding of said bead alters the signal at said one or more sensory elements;
(ib) ligating said complementary probe to said polynucleotide;
(ii) sequentially applying each of the cleavage means specific to each different cleavage-sensitive portion or linker until said bead is released from said polynucleotide to identify which complementary probe bound to said polynucleotide to determine said one or more bases to be sequenced;
(iii) optionally, restoring the probe which bound to said polynucleotide to its original pre-polynucleotide binding form;
(iv) optionally, modifying said polynucleotide to reveal the next base or more than one base for sequencing;
wherein, either in step (ii) or step (iv) an enzyme capable of removing at least part of the ligated complementary probe and at least one base of the polynucleotide being sequenced is added, and
(v) repeating each cycle of steps (i) to (iv) one or more times and in each cycle one or more bases of said sequence are identified.

Optionally during said method, the polynucleotide may be contacted with one or more complementary, unlabeled bases.

In comparison to the general method described hereinbefore, the use of cleavage enzymes in the above method is mandatory. Such cleavage enzymes are optional in previously disclosed methods, but may preferably be the cleavage means of choice in such methods.

Preferably the enzyme used in this method and the cleavage enzyme used in other methods of the invention is a nuclease, e.g. a restriction enzyme, which has a cleavage site separate from its recognition site and said probe contains a recognition site for said nuclease. In this case cleavage results in the removal of one or more bases from the target polynucleotide. This allows the method to be repeated. Optionally each test probe has a recognition site for a different nuclease. When the enzyme is the cleavage means used in the method of the invention different enzymes are required for each different sub-set of probes/bases.

When a complementary base is used, it may be a terminating nucleotide added to the end of the extending chain by polymerisation. This base may bind adjacent to the probe which binds to the target polynucleotide.

In methods in which complementary bases are also employed, these bases may be used to bind to the target sequence at the free 3' end (wherein the probe binds downstream from this site) and may be attached by polymerisation using an appropriate polymerase.

In this case, the base is not complementary to a base to be sequenced, and instead is used, for example, to complete the double stranded section to be cleaved. In that case all 4 possible bases may be used in the reaction at the same time and the sequence is determined based on which test probe binds. In that case in the above method a polymerase may also be used in step (i). The test probe is bound to the target polynucleotide by ligation. The incorporated base is removed on cleavage with at least a portion of the test probe (preferably all of the test probe).

In such methods, to allow performance of the stepwise ligation and cleavage method a test probe must bind during the method and thus in step (i) said test complementary probe is covalently bound to said polynucleotide by ligation.

Whilst in a preferred aspect the probe includes the one or more complementary nucleotides to the one or more nucleotides to be detected, the method also encompasses use of bead-attached nucleotides and a free probe which may be ligated to that nucleotide to provide the nuclease recognition site. In that case binding of the bead may be assessed to see if it is attached to the target polynucleotide before cleavage and/or after cleavage.

The test probe used in the method of the invention for stepwise ligation and cleavage preferably comprises a double stranded portion which may contain a recognition site for a nuclease and may further have a protruding strand (or single stranded part) which can form a duplex with a complementary protruding strand of the polynucleotide. In this way, probes will ligate to polynucleotides which have complementary protruding parts. The polynucleotide sequence may be determined by virtue of the change of signal during the various steps of the method. After ligation of the probe, a cleavage step is conducted, e.g. by a nuclease recognising a sequence within the probe to cleave the ligated complex at a site one or more nucleotides from the ligation site along the polynucleotide, leaving an end which may participate in any further cycle of ligation and/or polymerisation. This cleavage may be the cleavage which is the cleavage which allows bead release and/or may be the cleavage which reveals the next base for sequencing.

As is known in the art, in methods reliant on the introduction of a recognition site to allow cleavage, sequencing may be affected if the recognition site appears in the target sequence. This problem could be avoided by cleaving the targets with the same restriction enzyme or one with the same recognition sequence before the targets are immobilized (unless the restriction enzyme is the cleavage means as in that case multiple restriction enzymes are required). Alternatively this problem may be avoided by methylation of the target sequence.

In this method and other methods in which one or more cleavage enzymes is used a restriction enzyme as described hereinbefore may be used (type IIs or type IIb). Preferably a Type IIs restriction enzyme is employed to generate a 1, 2, 3 or 4 base overhang on cleavage. Preferred enzymes as described herein are preferably used for each cleavage enzyme employed in methods of the invention, e.g. in a preferred aspect the methods employ four Type IIs restriction enzymes which generate a 1, 2, 3 or 4 base overhang on cleavage. Preferably when multiple restriction enzymes are used in methods of the invention they each generate the same number of bases overhang on cleavage.

In determining whether a bead has bound to the polynucleotide via a probe, detection steps as described hereinbefore may be used. Thus, the presence or absence or level of signal associated with the bead may be detected. In particularly preferred aspects according to the invention, a quantitative assessment is made to determine the level of signal (from the bead) before and after the various cleavage steps.

As with other methods of the invention, the sub-sets of probes are distinguishable by their cleavage-sensitive linkers or portions, which in the present method may be the cleavage-sensitive portions which allow cleavage to release the next base(s) for sequencing.

Probes are distinguished on the basis of their recognition sites in those probes or other cleavage-sensitive portion/linkers. Thus for example, when the probes are distinguished on the basis of their recognition sites in those probes, each sub-set of probes has a different recognition site. In that case after binding of the bead to the polynucleotide, successive restriction enzymes are used which are directed to specific probe recognition sites. Release by a particular restriction enzyme is indicative of the relevant probe binding and hence the identity of the target sequence/base. For example, the method may use 2, 3, or more restriction enzymes with the same number of bases in the overhang, in succession, with detection of bead associated with the target performed before and after each addition. In the case of 4 different probe sub-sets, each could be distinguished by a different recognition site and the presence or absence of a probe from each probe sub-set could be determined by successive cleavage reactions.

In an alternative method, the enzyme which reveals the next base for sequencing is not the cleavage means which releases the bead. In such a method, for example, the probes may be attached to the bead via cleavage-sensitive linkers. The probe which bound may then be determined by successive cleavage steps using the different cleavage means specific to the different cleavage-sensitive linkers. Following this step which allows identification of the base(s) to be sequenced in that cycle, the polynucleotide may be made ready for the next cycle by use of the cleavage enzyme which reveals the next base for signalling.

As mentioned above, the step of determining which test complementary probe has bound by assessing the absence or presence of the bead or level of signal associated with the bead may be conducted at various points in the method. Thus for example the signal of the bead may be determined before, during and/or after step (i) and before, during and/or after each cleavage step using the different cleavage means.

In a preferred aspect, the cleavage means are enzymes as described hereinbefore which both serve for identification of the probe which has bound during step (i) but which also reveal the next base for sequencing. Thus in this case multiple cleavage enzymes are used sequentially in the cleavage step. Thus a first enzyme is used in the cleavage step, followed by a second enzyme and so forth until all enzymes specific for each cleavage-specific linker or portion has been used, or the bead has been released. Thus for example, when a single base is to be sequenced, four enzymes may be used in the cleavage step, i.e. a first, second, third and fourth enzyme is used, all of which enzymes are different and specific for said first, second, third or fourth probes by virtue of their distinct cleavage-specific linker or portion.

In accordance with this aspect of the invention, the probe is cleaved by an enzyme specific to that probe. Thus, conveniently the probe contains at least one recognition site for a cleavage enzyme.

The "enzyme capable of removing at least part of said complementary probe" is a cleavage enzyme which recognizes and binds to the probe when bound to the target nucleotide sequence and cleaves the probe and/or a sequence adjacent to said probe on the target polynucleotide, but may not necessarily bind to or cleave said probe when not bound to the target nucleotide sequence. When said enzyme cleaves the test probe, the cleavage effectively cleaves and hence removes the cleaved part of the probe from the target polynucleotide:probe complex. When said enzyme cleaves an adjacent sequence, the cleavage occurs upstream or downstream of said probe such that the probe (in its entirety) and some of the target polynucleotide sequence is removed from the target polynucleotide:probe complex on cleavage. The cleavage and recognition sites are preferably separate. Whilst the recognition site consists of at least a portion of the probe sequence, the cleavage site may not contain any of the probe sequence, e.g. when the cleavage site is up or downstream of the recognition site, e.g. when the enzyme is a restriction enzyme.

The cleavage site may be between the bead and the rest of the probe which binds to the target polynucleotide to be sequenced. In that case, if necessary, to allow reiterative sequencing reactions and as described above, a further cleavage enzyme may be necessary to remove the remaining portion of the probe and at least a part of the target sequence to reveal a new base(s) for sequencing. Conveniently, however, the cleavage site is located such that on cleavage the probe is removed in full from the target polynucleotide:probe complex as well as at least one base of the target polynucleotide.

Preferably said enzyme is a nuclease as described hereinbefore and each probe sub-set has a recognition site for a different nuclease.

Thus, in a preferred embodiment of the invention, each enzyme (preferably which enzyme is a cleavage means) is a nuclease which has a cleavage site separate from its recognition site and said test probe contains a recognition site for said nuclease and each enzyme used in said method has a different recognition site. The cleavage site of the enzymes may be the same or different. Preferably, as discussed above, said enzyme is a restriction enzyme, preferably a type IIb restriction enzyme and each enzyme used in said method is a different restriction enzyme.

By way of example, the method may be put into practice as follows. Firstly, the bead is prepared and a tether is attached as well as probe sets or bases for the sequencing reaction (e.g. using polyT beads and polyA tethers and probes). The bead should then be bound to the chip via the tether. The probes on the beads should be blocked to avoid beads binding to one another. These blocks may be released once target polynucleotides are in place. Adapters to the probes may be used as described herein and these may be maintained in non-reactive form until the time of use. Blocking moieties may be removed by fluid flow.

The target polynucleotide should then be isolated and prepared for sequencing. This may include the attachment of relevant DNA adapters (see the Example) to introduce sequences which provide specific functionality, e.g. to allow binding to the probes and/or tether. The target polynucleotide should then be attached to the solid support either directly or indirectly as described hereinbefore but avoiding contact with the bead until the sequencing reaction is begun.

The sequencing method is conducted in an aqueous reaction mix. The signal associated with the bead is determined while the bead is in the tether-only position. The bead is then allowed to contact the target polynucleotide (e.g. by a change in liquid flow or the application of magnetism) under conditions which allow binding between the probes/bases and the polynucleotide such that one of the probes or bases on the bead binds to the polynucleotide. Enzymes necessary for achieving covalent binding (e.g. ligases or polymerases) may be added simultaneously or before or after the bead is allowed to contact the target polynucleotide. Alternatively chemical ligation is performed. Once covalent binding has been achieved, the complexes may be washed to remove excess reagents. The signal is then determined. Release of the beads is then performed as described hereinbefore, e.g. by chemical or enzymatic, sequentially with a cleavage means specific to each cleavage-sensitive linker or portion. After each cleavage step with each cleavage means washing may be performed to remove excess reagent before the next step. The signal is determined at the end of each cleavage step involving a different cleavage means. In the case of ligation/cleavage sequencing the cleavage means may be restriction enzymes. When the bead is released in one of the cleavage steps the identity of the one or more bases to be sequenced may be determined.

Once all the cleavage means have been used or the identity of the bases(s) has been determined, a cycle of sequencing is considered completed. Once the cycle is completed and the one or more bases to be sequenced in that cycle has/have been determined, the cycle may be repeated. Thus preferably the methods as described hereinbefore include the steps of adding the relevant enzyme, washing the complexes to remove unbound enzyme and/or other reagents. Before completing the next cycle, optionally the probe, where used, may be restored and/or the polynucleotide may be modified to reveal the next base(s) in the polynucleotide to be sequenced (unless this was achieved in the cleavage step).

The invention also provides an apparatus for sequencing a single polynucleotide, wherein said apparatus comprises:
  a) a solid support comprising a surface with one or more sensory elements;
  b) a bead attached to said solid support by a tether;
  c) a set of probes or a set of bases attached to said bead,
    wherein each base or probe is optionally attached to said bead via a linker,
    wherein said set of probes or set of bases comprises at least one complementary probe or base for each possible permutation of one or more consecutive bases,
    wherein said complementary probe comprises at least a portion which may be complementary to a region of a polynucleotide comprising said one or more consecutive bases,
    wherein each at least one complementary probe or base contains a cleavage-sensitive portion or is attached to said bead via a cleavage-sensitive linker and the cleavage-sensitive portion or linker in the at least one complementary probe or base for each of the different possible permutations is different and can be cleaved by a cleavage means specific to said cleavage-sensitive linker or portion.

The various elements of the apparatus are as provided above in relation to the method of the invention. In particular, preferably said cleavage-sensitive portion or linker can be cleaved by an enzyme, preferably as defined hereinbefore. Furthermore, the probes, bead, sensory elements, solid support, tether and/or polynucleotide are as described hereinbefore.

The present invention also provides a kit comprising the above described apparatus as well as enzymes for cleaving the cleavage-sensitive portions or linker and/or an enzyme for restoring the probe to its original pre-polynucleotide binding form and/or an enzyme for removing at least part of the complementary probe and at least one base of the oligonucleotide being sequenced if that probe binds to the polynucleotide as described hereinbefore.

The invention will now be described by way of a non-limiting Example with reference to the drawings in which:

FIG. 1 shows the principle of the method of the invention illustrated in relation to a stepwise ligation and cleavage method. Stationary beads on the surface can cast a shadow or not on the pixels (dark area below the surface), depending on whether or not they are ligated to the target DNA (short light grey molecule attached to the silanized surface). The beads are positioned with a magnetic field (dark hatched lines), and the angle between the light (light hatched lines) and the magnetic field should be 90 degrees for optimal shadow/no shadow conditions.

Figure 2:
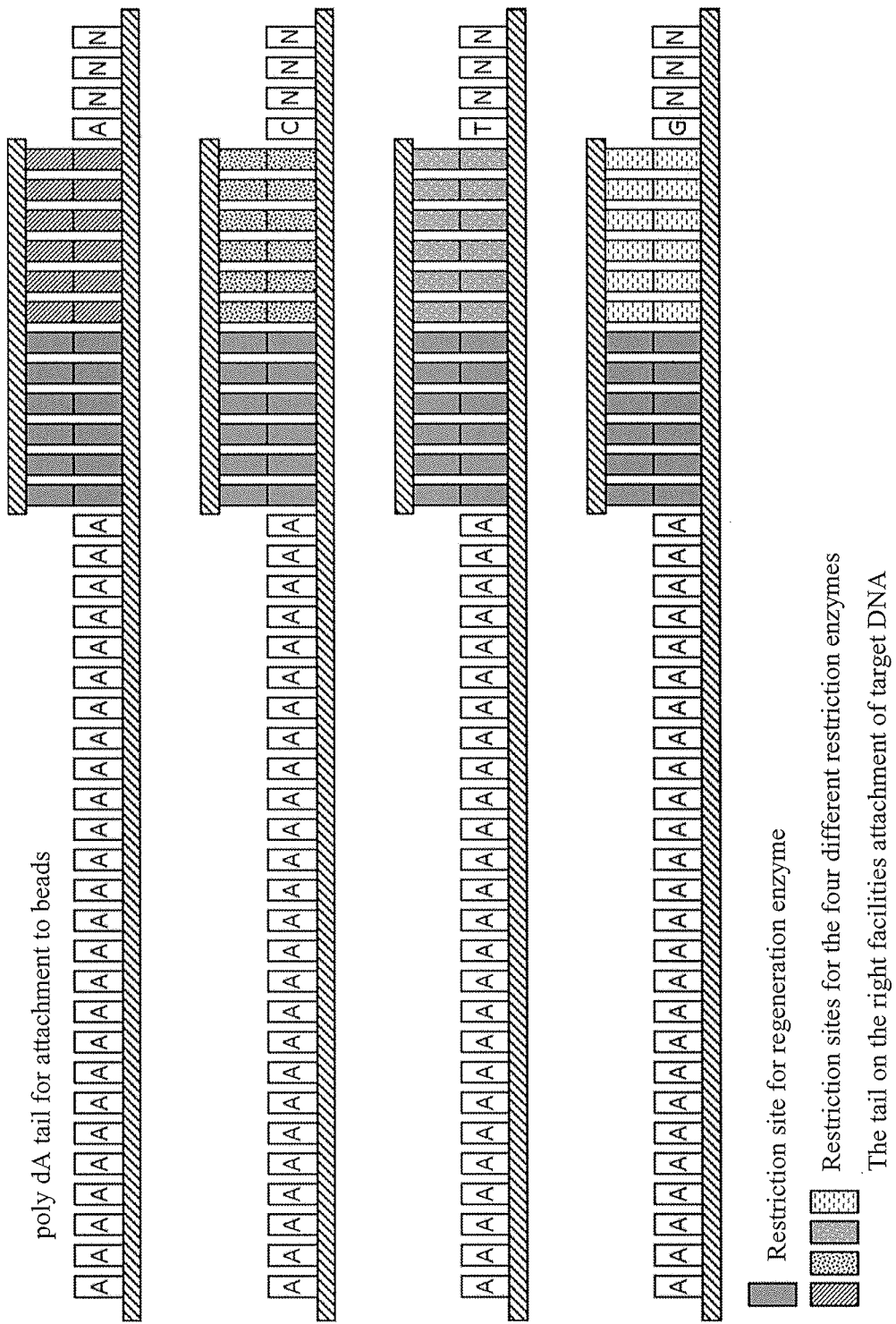

FIG. 2 illustrates the four different probe sub-sets. The innermost site on the overhang defines the sub-set, i.e. complementary to the target nucleotide, i.e. C, G, A or T, while the other three bases can be random. A total of 256 different probes are required to provide all possible permutations for a four base pair overhang (64 in each sub-set). Each probe has a single stranded polyA tail (SEQ ID NO:7) to allow for annealing to the polyT DNA-strands on the beads. In this example, each probe also contains two different recognition sites. The double stranded site which is dark in colour illustrates the recognition sequence for the regeneration enzyme, while the recognition site for the four different enzymes used for sequencing appear in the lighter double stranded region and are different for each different sub-set, i.e. specific to the A, C, T or G shown in the figure.

Figure 3:
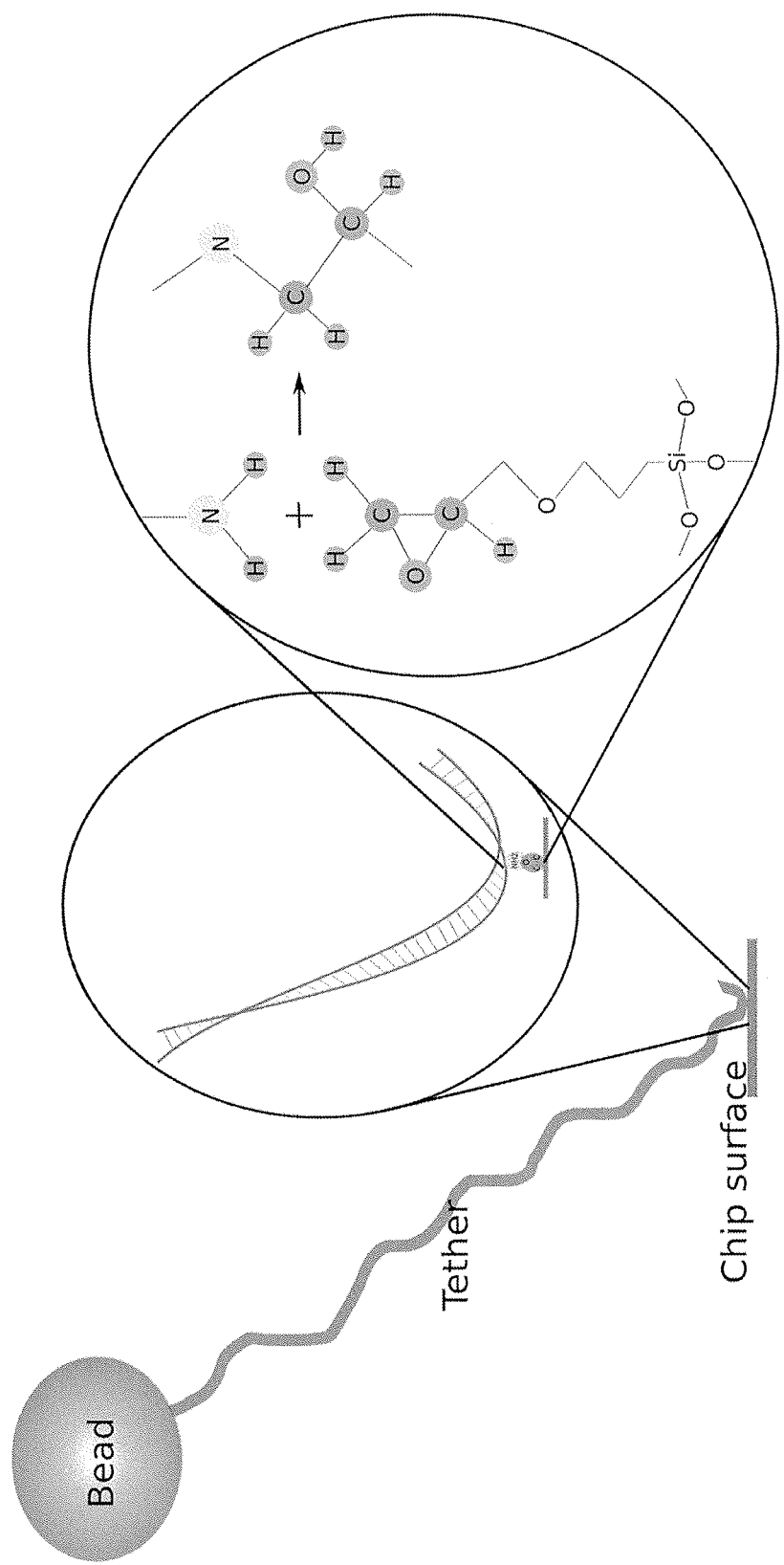

FIG. 3 shows an example of the attachment of the beads to the chip. The target DNA may be attached to the surface directly or through the tether. The close-up shows the mechanism of binding the tether to the chip.

Figure 4:
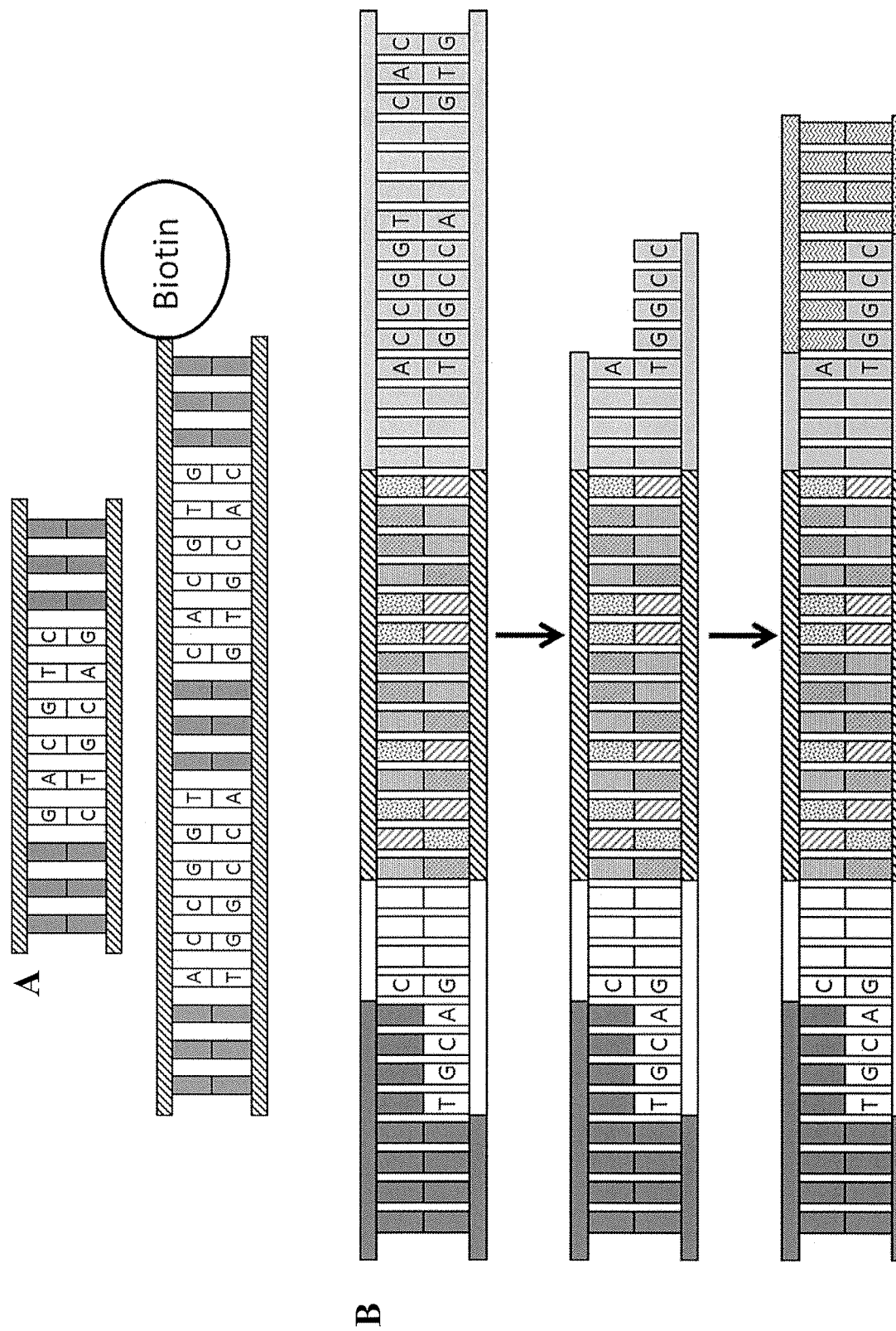

FIG. 4 shows the adapters used for attachment to the target DNA. A) Top figure, Adapter 1 has a recognition site for the enzyme AatII, giving a four base overhang when cut. Lower figure, Adapter 2 has two recognition sites; one for PmlI creating a blunt end, and one for AgeI creating a four base overhang. It further contains a biotin to allow for selecting DNA containing this adapter. B) Top figure, ligation of the target DNA (central portion, only 14 of the about 600 nt are shown) to the short end of the tether (5' end, black) is shown. Middle and lower figures, after cleavage of the adapter ligation to the probe (3' end) is possible.

Figure 5:
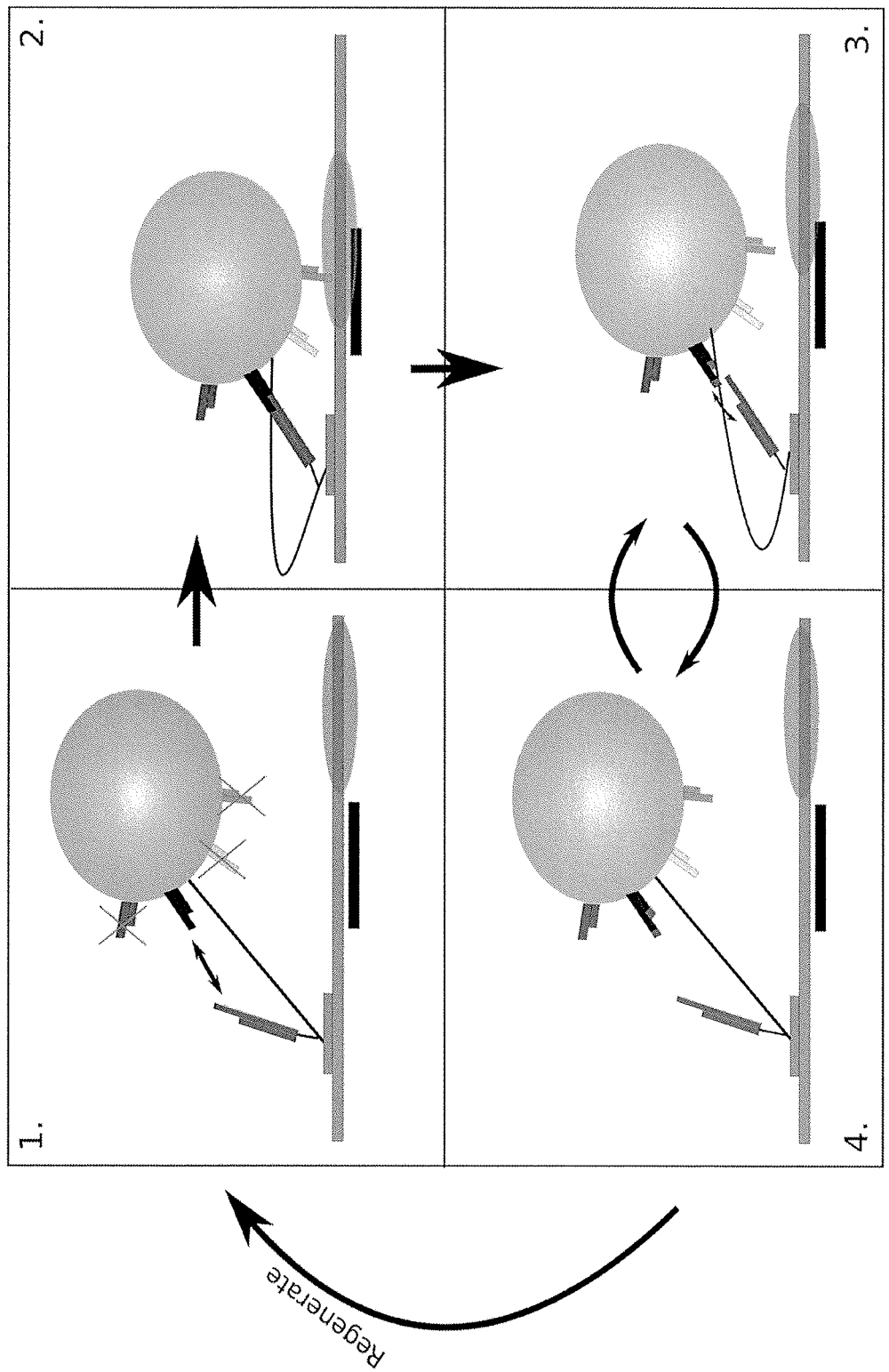

FIG. 5 illustrates the reiterative DNA sequencing cycle. 1. DNA is not ligated to probe/bead; no shadow on the pixel. 2. The DNA is ligated to the complementary probe; shadow on pixel. 3. The enzyme specific for the complementary probe will cut the target DNA, leaving one extra base on the probe. 4. The bead is bound only to the tether casting no shadow on the pixel.

Figure 6:
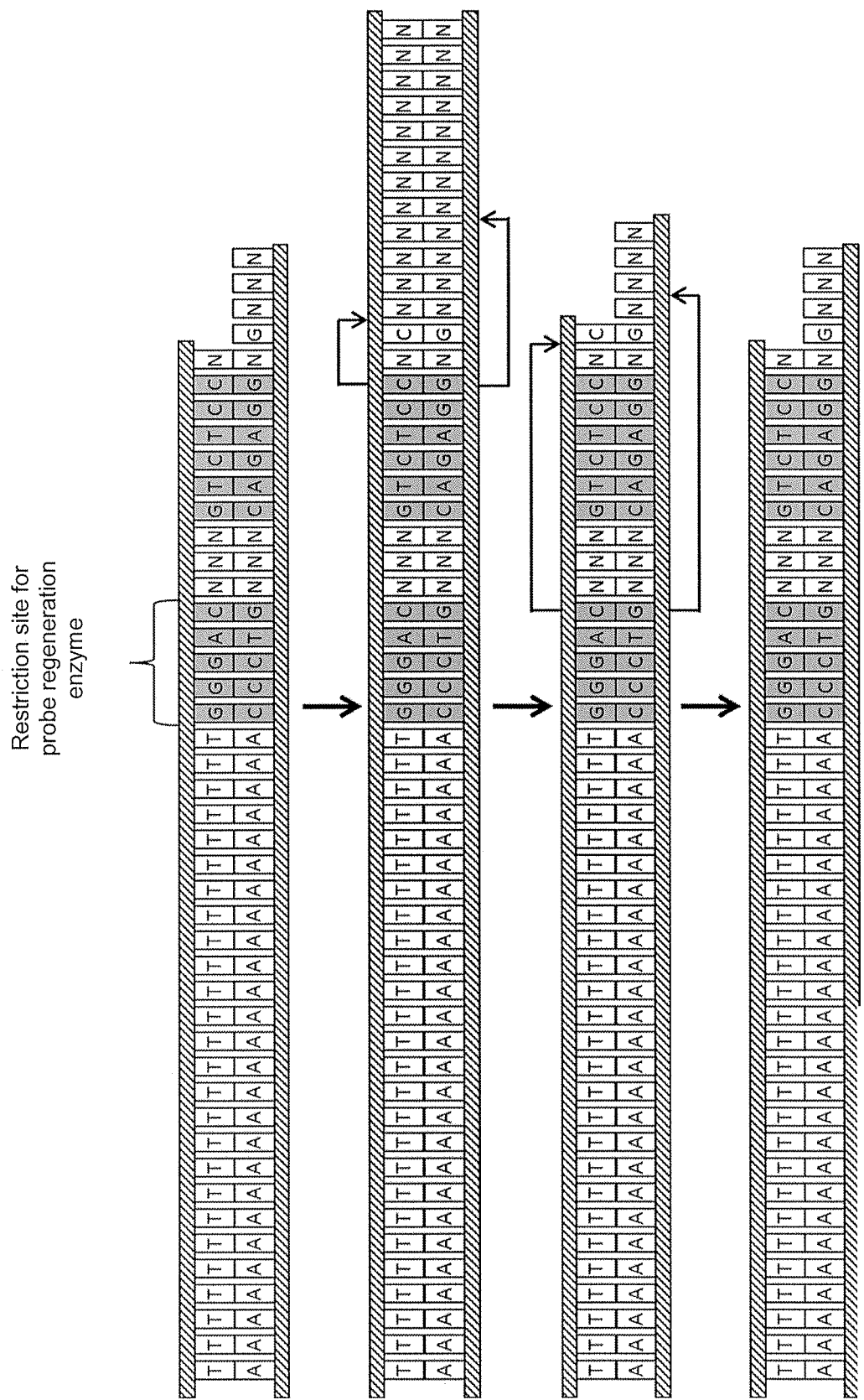

FIG. 6 shows the method of regenerating the probes. The topmost figure shows the probe attached to the magnetic bead with a dT25 overhang. In the next step the target DNA is ligated to the DNA, followed by cleavage with a restriction enzyme (cleavage site indicated), leaving one extra base on the probe, making it useless for further sequencing as it would incorrectly identify the base being sequenced. In the last step, the probe is regenerated by a restriction enzyme (the recognition site is shown in the light grey region) thereby removing the extra base. The sequences appearing in FIG. 6, in order from the top of the page to the bottom, are as follows: upper strand-SEQ ID NO:1 and lower strand-SEQ ID NO:2; upper strand-SEQ ID NO:3 and lower strand-SEQ ID NO:4; upper strand-SEQ ID NO:5 and lower strand-SEQ ID NO:6; upper strand-SEQ ID NO:1 and lower strand-SEQ ID NO:2.

Each of the features described in the Example, are preferred aspects which may be considered as preferred features in combination with any of the embodiments described hereinbefore.

EXAMPLE 1: SEQUENCING BY SEQUENTIAL LIGATION AND CLEAVAGE

Preparation of the Apparatus

Methods of preparing an apparatus with a silanized image chip are described in WO2012/042052 which is incorporated herein by reference. The silanized surface has exposed epoxy group allowing the attachment of DNA molecules via spontaneous reaction between the epoxy group and the terminal amine groups of the DNA molecules.

Materials

Bead:

1 μm Dynabeads with 25 mers of single stranded homopolymeric DNA (polyT).

Tether:

An 1800 bp DNA-tether carrying a polyA tail.

The tether does not contain recognition sites for any enzymes that are to be used in sequencing. It is produced by PCR, has a balanced nucleotide content and no repeats or hairpin structures.

The primers used in its preparation each contain a recognition site. The tether is initially attached to non-magnetic beads by the end that will later attach to the chip. The first recognition site creates an overhang to attach to the polyT oligonucleotides on the bead. The second recognition site creates an overhang to which the target DNA may be attached. An internal amine-group on one of the primers used during PCR enables binding to the silane on the chip.

Probes:

A set of probes is used in which each possible permutation for the overhang on the molecule to be sequenced to which the probes will bind is represented. In the present method, the overhang is 4 bases in length and thus there are 256 possible permutations. However, in each sequencing round only one base is detected. Thus within the set of probes there are 4 sub-sets, wherein each sub-set is directed to a different base to be detected but includes all the permutations necessary to bind the overhang (e.g. NNNA).

The probes used in the method are shown in FIG. 2. These probes are all bound to the bead via their polyA tails (SEQ ID NO:7). The probes are made by annealing two short synthetic single stranded DNA molecules. Only the shortest of these molecules will be 5'-phosphorylated in order to avoid bead-to-bead ligation through the probes. A blunt end at the variable side may increase the stability during production of chips and in transport to the end user and extend the time before expiration of the chips, but has not been shown in the Figure.

Each of the probes contains two restriction enzyme sites (Type IIS) for enzymes which are blocked by methylation. One of the enzymes is used to regenerate the probes. The second is specific for the sub-set of probes which bind to a specific base to be sequenced in the overhang. In this case only one base is to be sequenced in each cycle and thus four different enzymes and sub-sets of probes are needed.

Attachment of the Tether to the Beads

The bead and the purified DNA tether are mixed and annealed. A DNA polymerase is used to extend the A-tail using the polyT as template. Finally a DNA ligase is used to close the gap. Appropriate techniques are used to ensure that only one strand of DNA is covalently bound to the bead.

Attachment of the Probes to the Bead

The mixture of all probes is added to the bead carrying the tether, annealed through the long polyA/polyT, and the gap is sealed using T4 DNA ligase. This provides beads carrying thousands of probes.

Attachment of the Bead to the Chip.

The beads are attached to the chip through the tether. The bead is attached to the surface by a reaction between an epoxide on the silanized chip and an internal, but close to one end, amine group on the DNA tether (see FIG. 3). A magnet is used to remove and rotate non-bound beads such that each pixel has a bound DNA tether.

Preparation of the DNA Molecule for Sequencing

The DNA that is to be sequenced is prepared as follows:

1. Fragment the DNA by sonication and select an appropriate size (<600 nt); 1 kb DNA is approximately 340 nm, thus ensuring a sufficient size difference between the target DNA and tether.

2. Methylate the DNA to make it resistant to restriction enzymes to be used in sequencing (CpG-, dam-, or specific methylases for the restriction enzymes used for preparing and sequencing the DNA).

3. Repair ends and phosphorylate.

4 Ligate adapters to both ends of each DNA, and select the correct molecules.

The adapters to be used are shown in FIG. 4a. Both adapters are dephosphorylated to avoid self-ligation. The top adapter, Adapter 1 contains a recognition site for an enzyme that creates a 3'-overhang and is blocked by CpG-methylation, e.g. AatII. This adapter will, after cutting with AatII, provide an overhang that can be ligated to the short end of the tethers on the chip. Adapter 2 contains one biotinylated end, while the other end contains recognition sites for two enzymes blocked by CpG methylation; one that creates a blunt end, e.g. PmlI, and one that that creates a 5'-overhang, e.g. AgeI. The AgeI-site is closest to the non-biotinylated end.

The DNA and the adapters are mixed and ligated. After ligation only 50% of the DNA will have different adapters at each end, the other will have either just adapter 1 or just adapter 2. DNA containing adapter 2 can be selected for by binding the DNA to magnetic beads containing streptavidin. After unbound molecules are removed, DNA can be released from the beads by restricting with PmlI. Simultaneously restriction cutting with AatII will create staggered ends on adapter 1.

5. Ligation of DNA to the tether. The shortest end of the tether is cut using the same enzyme that cuts the adapter (e.g. AatII). This enzyme should yield the opposite overhang as those of the probes to avoid ligation to the probes Then the AatII-restricted adapter-DNA-adapter may be ligated to the tether. Since only adapter 1 can be ligated to the tether, this step will also ensure that only DNA with that adapter ligated to it will be used in this step.

FIG. 4B shows the target DNA attached to the tether (top figure) in which the black region shows the tether, the central portion the target NDA and the region at the 3' end has the adapter.

6. Then the restriction enzyme AgeI is used to create a staggered end on adapter 2 such that it is available for binding to a probe with a complementary overhang (see FIG. 4B, middle figure). If blunt-ended probes are used, these must first be converted to staggered ends using the regeneration enzyme.

Sequencing Method

The following steps (FIG. 5) are repeated until the entire DNA is sequenced:

1. Ligate probe to DNA; the DNA will attach to the probe with the correct complementary overhang (see FIG. 6, boxes 1 and 2 and see FIG. 4B, final figure).

2. Assess level of light falling on pixel. This will show which DNA has not been ligated, and thus should not be considered cut after step 4. The DNA may be ligated in the next round.

3. Add the first restriction enzyme. After the reaction the enzyme needs to be removed or inactivated.

4. Assess level of light falling on pixel.

5. Repeat 3 and 4 with the three other restriction enzymes to test for the other three bases (see FIG. 5, boxes 3 and 4).

6. Regenerate probes using the fifth enzyme (described below), assess level of light falling on pixel.

Regeneration of Probes to Original Pre-Binding Form

As illustrated in FIG. 6, after one round of ligation and cutting the probes will no longer be specific for the correct base and therefore need to be regenerated. The first figure in FIG. 6 shows the probe before binding, the second figure shows the probe when bound to the target, the third figure shows the modified probe which results after cleavage to release the probe from the target polynucleotide which is not the same as the probe pre-binding.

This problem is solved by using probes which have a second recognition site that can be used to regenerate the probes prior to each ligation. The final figure in FIG. 6 shows regeneration of the probe by use of the enzyme to the second recognition site. Since many probes are present on the bead, the probability of reusing a probe is low and regeneration is performed only periodically.

The invention claimed is:

1. A method for determining a nucleotide sequence of a single polynucleotide, wherein:
   a) said polynucleotide is immobilised on a solid support;
   b) said solid support comprises a surface with one or more sensory elements;
   c) a bead is attached to said solid support by a tether;
   d) a set of probes or a set of bases is attached to said bead, wherein each base or probe is optionally attached to said bead via a linker,
      wherein said set of probes or set of bases comprises at least one complementary probe or base for each possible permutation of the one or more bases to be sequenced in each cycle of said method,
      wherein said complementary probe comprises at least a portion which may be complementary to a region of said polynucleotide comprising said one or more bases to be sequenced,
      wherein each at least one complementary probe or base contains a cleavage-sensitive portion or is attached to said bead via a cleavage-sensitive linker and the cleavage-sensitive portion or linker in the at least one complementary probe or base for each of the different possible permutations is different and can be cleaved by a cleavage means specific to said cleavage-sensitive portion or linker;
   and wherein said method comprises the steps of:
      contacting said polynucleotide with said bead such that the complementary base which is complementary to said one base to be sequenced or the complementary probe which comprises at least a portion which is complementary to said region comprising said one or more bases to be sequenced binds to said base or said region comprising said one or more bases in said polynucleotide and covalently binding said complementary probe or base to said polynucleotide, wherein binding of said bead alters the signal at said one or more sensory elements;

(ii) sequentially applying each of the cleavage means specific to each different cleavage-sensitive portion or linker until said bead is released from said polynucleotide to identify which complementary base or probe bound to said polynucleotide to determine said one or more bases to be sequenced;

(iii) optionally, when a set of probes is used, restoring the probe which bound to said polynucleotide to its original pre-polynucleotide binding form;

(iv) optionally, modifying said polynucleotide to reveal the next base or more than one base for sequencing; and (v) optionally repeating each cycle of steps (i) to (iv) one or more times and in each cycle one or more bases of said sequence are identified.

2. The method as claimed in claim 1, wherein a) at least two cycles are performed; b) the covalent binding of the complementary base and/or the probe is by ligation or polymerization; and/or c) the method is one of sequencing by synthesis, sequencing by ligation or sequencing by stepwise ligation and cleavage.

3. The method as claimed in claim 1, wherein said method is a method of sequencing by synthesis, wherein:

a set of bases is attached to said bead, wherein each base is attached to said bead via a linker, wherein said set of bases comprises at least one complementary base for each possible permutation of the base to be sequenced in each cycle of said method, wherein each at least one base is attached to said bead via a cleavage-sensitive linker and the cleavage-sensitive linker in the at least one complementary base for each of the different possible permutations is different and can be cleaved by a cleavage means specific to said cleavage-sensitive linker;

and wherein said method comprises the steps of:

contacting said polynucleotide with said bead such that the complementary base which is complementary to said base to be sequenced binds to said base and covalently binding said complementary base to said polynucleotide, wherein binding of said bead alters the signal at said one or more sensory elements;

(ii) sequentially applying each of the different cleavage means specific to each different cleavage-sensitive linker until said bead is released from said polynucleotide to identify which complementary base bound to said polynucleotide to determine said base to be sequenced;

(iii) optionally, modifying said polynucleotide to reveal the next base for sequencing; and (iv) repeating each cycle of steps (i) to (iii) one or more times and in each cycle one base of said sequence is identified.

4. The method as claimed in claim 1, wherein said method is a method of sequencing by stepwise ligation and cleavage, wherein:

a set of probes is attached to said bead, wherein each probe is optionally attached to said bead via a linker, wherein said set of probes comprises at least one complementary probe for each possible permutation of the one or more bases to be sequenced in each cycle of said method, wherein said complementary probe comprises at least a portion which may be complementary to a region of said polynucleotide comprising said one or more bases to be sequenced, wherein each at least one complementary probe contains a cleavage-sensitive portion or is attached to said bead via a cleavage-sensitive linker and the cleavage-sensitive portion or linker in the at least one complementary probe for each of the different possible permutations is different and can be cleaved by a cleavage means specific to said cleavage-sensitive linker or portion;

and wherein said method comprises the steps of:

(ia) contacting said polynucleotide with said bead such that the complementary probe which comprises at least a portion which is complementary to said region comprising said one or more bases to be sequenced binds to said region comprising said one or more bases in said polynucleotide, wherein binding of said bead alters the signal at said one or more sensory elements;

(ib) ligating said complementary probe to said polynucleotide;

(ii) sequentially applying each of the cleavage means specific to each different cleavage-sensitive portion or linker until said bead is released from said polynucleotide to identify which complementary probe bound to said polynucleotide to determine said one or more bases to be sequenced;

(iii) optionally, restoring the probe which bound to said polynucleotide to its original pre-polynucleotide binding form;

(iv) optionally, modifying said polynucleotide to reveal the next base or more than one base for sequencing; wherein, either in step (ii) or step (iv) an enzyme capable of removing at least part of the ligated complementary probe and at least one base of the polynucleotide being sequenced is added, and (v) repeating each cycle of steps (i) to (iv) one or more times and in each cycle one or more bases of said sequence are identified.

5. The method as claimed in claim 1, wherein said cleavage-sensitive portion or linker is cleaved by an enzyme.

6. The method as claimed in claim 4, wherein said enzyme is a nuclease which has a cleavage site separate from its recognition site and said complementary probe contains a recognition site for said nuclease.

7. The method as claimed in claim 6, wherein said enzyme is a restriction enzyme.

8. The method as claimed in claim 6, wherein said cleavage-sensitive portion is present in the complementary probe and cleavage by said nuclease specific for said complementary probe releases said bead and removes at least part of the ligated complementary probe and at least one base of the polynucleotide being sequenced.

9. The method as claimed in claim 1, wherein each probe in the set of probes contains a recognition site for a nuclease which has a cleavage site separate from its recognition site which on cleavage restores the probe to its original pre-polynucleotide binding form if that probe binds to said polynucleotide during said method.

10. The method as claimed in claim 9, wherein said probe contains two recognition sites;
   a recognition site for a nuclease which has a cleavage site separate from its recognition site which on cleavage restores the probe to its original pre-polynucleotide binding form if that probe binds to said polynucleotide during said method; and
   (ii) a recognition site for a nuclease which on cleavage removes at least part of the complementary probe and at least one base of the polynucleotide being sequenced if that probe binds to said polynucleotide.

11. The method as claimed in claim 1, wherein in step (ii) multiple enzymes each capable of cleaving a different cleavage-sensitive linker or portion are used sequentially.

12. The method as claimed in claim 1, wherein identifying which complementary base or probe of said set of bases or set of probes bound to said polynucleotide comprises determining the presence, absence or level of signal associated with said bead after each cleavage relative to the presence, absence or level of signal associated with said bead before each cleavage, wherein a change in the signal is indicative of binding of said complementary base or probe with the cleavage-sensitive linkage specific to the cleavage means used in said cleavage step.

13. The method as claimed in claim 12, wherein the level of signal associated with said bead before and after said cleavage step is determined and a decrease of signal after cleavage is indicative of binding of said complementary base or probe with the cleavage-sensitive linkage specific to the cleavage means used in said cleavage step.

14. The method as claimed in claim 1, wherein a) the radius of said bead is larger than the length of the polynucleotide;
   b) the bead is magnetic; and/or c) the complementary base or probe is terminating on the binding of further complementary bases or probes.

15. The method as claimed in claim 12, wherein a) said sensory elements are light sensitive elements; and/or b) said level of signal is determined by detecting light changes resulting from the presence of the bead on a light sensitive surface.

16. The method as claimed in claim 1, wherein a) said solid support is a chip; b) said tether is a nucleic acid molecule; c) said nucleic acid molecule is from 1000-2000 nucleotides in length; and/or d) said polynucleotide is attached to the solid support by the tether.

17. An apparatus suitable for sequencing a single polynucleotide, wherein said apparatus comprises:
   a) a solid support comprising a surface with one or more sensory elements;
   b) a bead attached to said solid support by a tether; and
   c) a set of probes or a set of bases attached to said bead, wherein each base or probe is optionally attached to said bead via a linker,
      wherein said set of probes or set of bases comprises at least one complementary probe or base for each possible permutation of one or more consecutive bases,
      wherein said complementary probe comprises at least a portion which may be complementary to a region of a polynucleotide comprising said one or more consecutive bases, and
      wherein each at least one complementary probe or base contains a cleavage-sensitive portion or is attached to said bead via a cleavage-sensitive linker and the cleavage-sensitive portion or linker in the at least one complementary probe or base for each of the different possible permutations is different and can be cleaved by a cleavage means specific to said cleavage-sensitive linker or portion.

18. The apparatus as claimed in claim 17, wherein said cleavage-sensitive portion or linker can be cleaved by an enzyme.

19. The apparatus as claimed in claim 17, wherein
   (i) said cleavage-sensitive portion is present in the complementary probe;
   (ii) the radius of said bead is larger than the length of the polynucleotide; and/or the bead is magnetic;
   (iii) said sensory elements are light sensitive elements;
   (iv) said solid support is a chip;
   (v) said tether is a nucleic acid molecule; and/or
   (vi) said polynucleotide is attached to the solid support by the tether.

20. A kit comprising an apparatus as claimed in claim 17 and enzymes for cleaving the cleavage-sensitive portion or linker and/or an enzyme for restoring the probe to its original pre-polynucleotide binding form and/or an enzyme for removing at least part of the complementary probe and at least one base of the oligonucleotide being sequenced if that probe binds to the polynucleotide.

* * * * *

SEQUENCE LISTING

<160> NUMBER OF SEQ ID NOS: 7

<210> SEQ ID NO 1
<211> LENGTH: 41
<212> TYPE: DNA
<213> ORGANISM: Artificial Sequence
<220> FEATURE:
<223> OTHER INFORMATION: chemically-synthesized sequence
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 1
tttttttttt tttttttttt tttttgggga cnnngtctcc n                41

<210> SEQ ID NO 2
<211> LENGTH: 45
<212> TYPE: DNA
<213> ORGANISM: Artificial Sequence
<220> FEATURE:
<223> OTHER INFORMATION: chemically-synthesized sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 2
nnngnggaga cnnngtccca aaaaaaaaaa aaaaaaaaa aaaaa             45

<210> SEQ ID NO 3
<211> LENGTH: 54
<212> TYPE: DNA
<213> ORGANISM: Artificial Sequence
<220> FEATURE:
<223> OTHER INFORMATION: chemically-synthesized sequence
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(54)
<223> OTHER INFORMATION: n is a, c, g, or t

<400> SEQUENCE: 3
tttttttttt tttttttttt tttttgggga cnnngtctcc ncnnnnnnnn nnnn  54

<210> SEQ ID NO 4
<211> LENGTH: 54
<212> TYPE: DNA
<213> ORGANISM: Artificial Sequence
<220> FEATURE:
<223> OTHER INFORMATION: chemically-synthesized sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

```
<400> SEQUENCE: 4
nnnnnnnnnn nngnggagac nnngtcccaa aaaaaaaaaa aaaaaaaaaa aaaa        54

<210> SEQ ID NO 5
<211> LENGTH: 42
<212> TYPE: DNA
<213> ORGANISM: Artificial Sequence
<220> FEATURE:
<223> OTHER INFORMATION: chemically-synthesized sequence
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 5
tttttttttt tttttttttt tttttggga cnnngtctcc nc                      42

<210> SEQ ID NO 6
<211> LENGTH: 46
<212> TYPE: DNA
<213> ORGANISM: Artificial Sequence
<220> FEATURE:
<223> OTHER INFORMATION: chemically-synthesized sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 6
nnnngnggag acnnngtccc aaaaaaaaaa aaaaaaaaaa aaaaaa                 46

<210> SEQ ID NO 7
<211> LENGTH: 26
<212> TYPE: DNA
<213> ORGANISM: Artificial Sequence
<220> FEATURE:
<223> OTHER INFORMATION: chemically-synthesized sequence

<400> SEQUENCE: 7
aaaaaaaaaa aaaaaaaaaa aaaaaa                                       26
```